(12) United States Patent
Margiott et al.

(10) Patent No.: US 11,800,999 B2
(45) Date of Patent: Oct. 31, 2023

(54) MEDICAL DEVICE WITH STABILITY MEASUREMENT REPORTING

(71) Applicant: ViOptix, Inc., Newark, CA (US)

(72) Inventors: Alex Michael Margiott, Andover, MA (US); Jordan Sweer, Fremont, CA (US); Kate LeeAnn Bechtel, Pleasant Hill, CA (US)

(73) Assignee: ViOptix, Inc., Newark, CA (US)

( * ) Notice: Subject to any disclaimer, the term of this patent is extended or adjusted under 35 U.S.C. 154(b) by 78 days.

(21) Appl. No.: 17/146,197

(22) Filed: Jan. 11, 2021

(65) Prior Publication Data

US 2021/0212610 A1 Jul. 15, 2021

Related U.S. Application Data

(60) Provisional application No. 62/959,808, filed on Jan. 10, 2020.

(51) Int. Cl.
*A61B 5/145* (2006.01)
*A61B 5/00* (2006.01)

(52) U.S. Cl.
CPC ........ *A61B 5/14542* (2013.01); *A61B 5/7221* (2013.01); *A61B 5/743* (2013.01); *A61B 2562/0219* (2013.01)

(58) Field of Classification Search
CPC ... A61B 5/14542; A61B 5/7221; A61B 5/743; A61B 2562/0219; A61B 5/02416;
(Continued)

(56) References Cited

U.S. PATENT DOCUMENTS 5,368,026 A * 11/1994 Swedlow ............... A61B 5/721
600/323
6,385,821 B1 5/2002 Modgil et al.
(Continued)

FOREIGN PATENT DOCUMENTS

WO WO2017185103 10/2017

OTHER PUBLICATIONS

Clarke, Geoffrey, Signal Quality Analysis in Pulse Oximetry: Modelling and Detection of Motion Artifact, May 2015, 107 pages, Ottawa-Carleton Institute for Biomedical Engineering Department of Systems and Computer Engineering Carleton University Ottawa, Ontario.

(Continued)

*Primary Examiner* — Eric F Winakur
*Assistant Examiner* — Abid A Mustansir
(74) *Attorney, Agent, or Firm* — Aka Chan LLP

(57) ABSTRACT

An oximeter device determines an oxygen saturation for the tissue and determines a quality value for the oxygen saturation and associated measurements of the tissue. The quality value is calculated from reflectance data received at the detectors of the oximeter device. An accelerometer of the oximeter device can detect movement of the oximeter device when oximetry measurements are made by the oximeter device. An amount of the movement is an indicator of a probe face of the oximeter device changing position with respect to the tissue when the measurements are made. The accelerometer information is used by the oximeter device to adjust the quality value to reflect the amount movement. The oxygen saturation and the adjusted quality metric value are displayed on a display of the oximeter device so that a user may view the quality of the displayed information.

19 Claims, 24 Drawing Sheets

(58) Field of Classification Search
CPC ............ A61B 2560/0425; A61B 5/002; A61B 5/0075; A61B 2562/166; A61B 5/14551
See application file for complete search history.

(56) References Cited

U.S. PATENT DOCUMENTS

| | | |
|---|---|---|
| 7,236,813 B2 | 6/2007 | Parker |
| 7,532,919 B2 | 5/2009 | Soyemi et al. |
| 8,233,955 B2 | 7/2012 | Al-ali et al. |
| 8,938,279 B1 | 1/2015 | Heaton, II et al. |
| 9,788,793 B2 | 10/2017 | Zong et al. |
| 10,786,187 B2 | 9/2020 | Bechtel et al. |
| 2004/0034294 A1* | 2/2004 | Kimball ............... A61B 5/6826 600/323 |
| 2006/0211925 A1 | 9/2006 | Lamego et al. |
| 2008/0242959 A1 | 10/2008 | Xu et al. |
| 2011/0205535 A1 | 8/2011 | Soller et al. |
| 2014/0046152 A1 | 2/2014 | Bechtel et al. |
| 2015/0230758 A1 | 8/2015 | Ochs |
| 2016/0084869 A1* | 3/2016 | Yuen ..................... A63B 60/46 73/510 |
| 2017/0303837 A1* | 10/2017 | Bechtel ............... A61B 5/7221 |
| 2020/0305777 A1 | 10/2020 | Kiani et al. |

OTHER PUBLICATIONS

Petterson, Michael T.; Begnoche, Valerie L.; Graybeal, John M., The Effect of Motion on Pulse Oximetry and Its Clinical Significance, Dec. 2007, pp. S78-S84, vol. 105, No. 6, Anesthesia & Analgesia, International Anesthesia Research Society.

International Search Report, PCT Application PCT/US2021/013005, dated May 10, 2021, 7 pages.

* cited by examiner

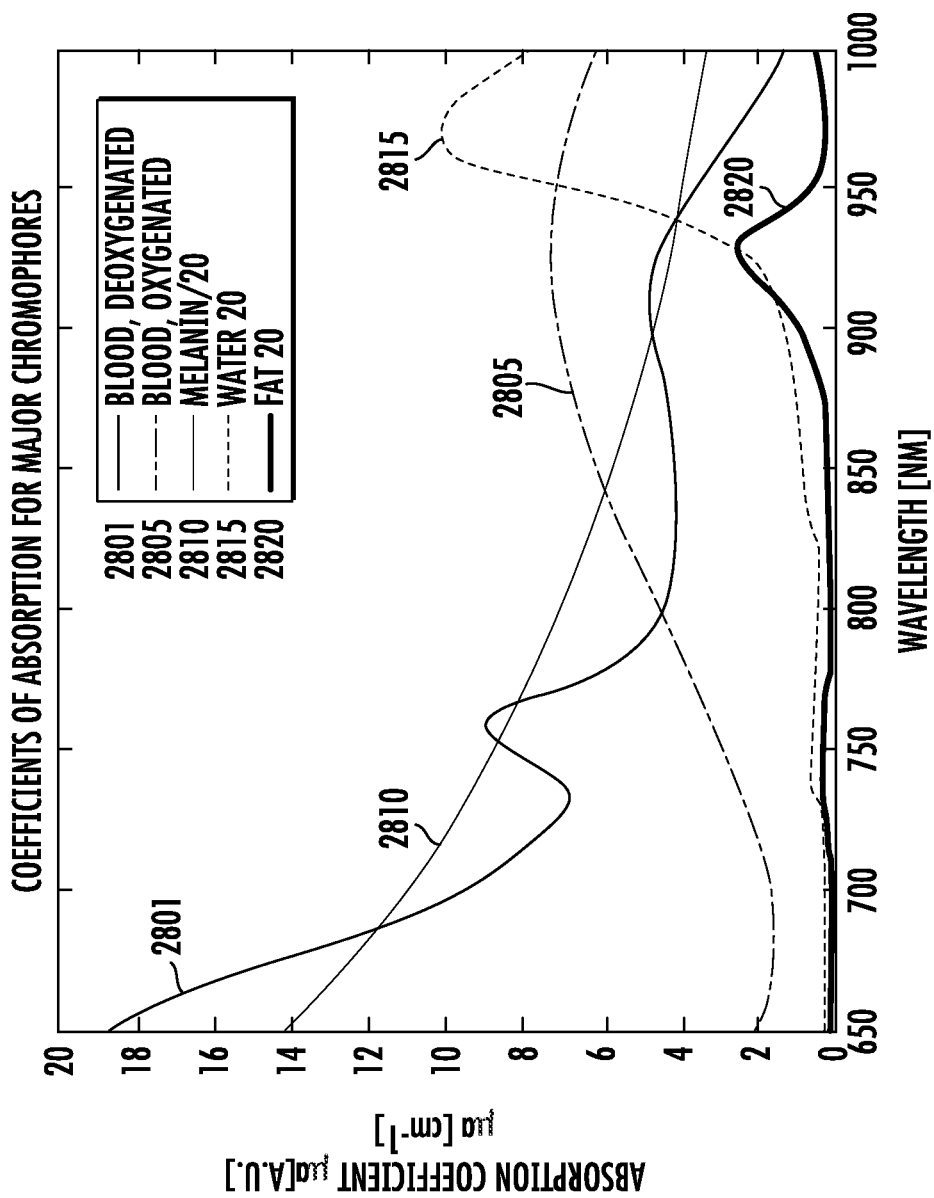

MEDICAL DEVICE WITH STABILITY MEASUREMENT REPORTING

CROSS-REFERENCE TO RELATED APPLICATIONS

This application claims the benefit of U.S. patent application 62/959,808, filed Jan. 10, 2020. This application is incorporated by reference along with all other references cited in these applications.

BACKGROUND OF THE INVENTION

The present invention relates generally to optical systems that monitor parameters related to oxygen levels in tissue. More specifically, the present invention relates to optical probes, such as compact, handheld oximeters, and sheaths for the optical probes that shield the optical probes from contaminants during use and communicate status information to the optical probes regarding contaminant protection so that the optical probes are reusable.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are the dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for an improved tissue oximetry devices and methods of shielding oximetry devices during use for reuse of the devices.

BRIEF SUMMARY OF THE INVENTION

Embodiments relate to compact, handheld oximeters and sheaths that house and shield the handheld oximeters from patient contact and contaminants during use and shield patients from contaminants on the handheld oximeters. Because a handheld oximeter is located in a sheath and cannot contaminate patient tissue, the handheld oximeter can be reused.

In an implementation, a method includes emitting light from at least one source of an oximeter device into a tissue to be measured, wherein the oximeter device comprises a nonvolatile memory that stores simulated reflectance curves and the nonvolatile memory retains the simulated reflectance curves even after the device is powered off, and receiving at a plurality of detectors of the oximeter device light reflected from the tissue in response to the emitted light.

The method includes generating, by the detectors, a plurality of detector responses from the reflected light and fitting the detector responses to the simulated reflectance curves stored in the nonvolatile memory to determine an absorption coefficient value for the tissue. The method incudes calculating an oximetry value for the tissue from the absorption coefficient value, and based on the absorption coefficient value, calculating a quality metric value for the oximetry value. The method includes detecting, by an accelerometer of the oximeter device, a movement of the oximeter device and adjusting the quality metric value based on the detected movement of the oximeter device to generate an adjusted quality metric value. The displaying may display the oximetry value and the adjusted quality metric value for the oximetry value.

An amount of the movement is an indicator of a probe face of the oximeter device changing position with respect to the tissue when the measurements are made. The accelerometer information is used by the oximeter device to adjust the quality value to reflect the amount movement so that when the adjusted quality value is displayed, a user may view the quality of the displayed information.

The handheld oximeters implementations are entirely self-contained, without any need to connect, via wires or wirelessly, to a separate system unit for making oximetry measurements. The sources and detectors of the oximetry device are arranged in an arrangement having various source-detector pair distances that allow for robust calibration, self-correction, and spatially-resolved spectroscopy in a compact probe. Other source-detector arrangements are also possible.

In an implementation, the handheld oximeter is a tissue oximeter that can measure oxygen saturation without requiring a pulse or heartbeat. A tissue oximeter of the invention is applicable to many areas of medicine and surgery, including plastic surgery. The tissue oximeter can make oxygen saturation measurements of tissue where there is no pulse; such tissue, for example, may have been separated from the body (e.g., a flap) and will be transplanted to another place in the body.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 28 shows a graph of the absorption coefficient $\mu_a$ versus wavelength of light for some significant tissue chromophores: blood containing oxygenated hemoglobin, blood containing deoxygenated hemoglobin, melanin, and water.

DETAILED DESCRIPTION OF THE INVENTION

Figure 1:
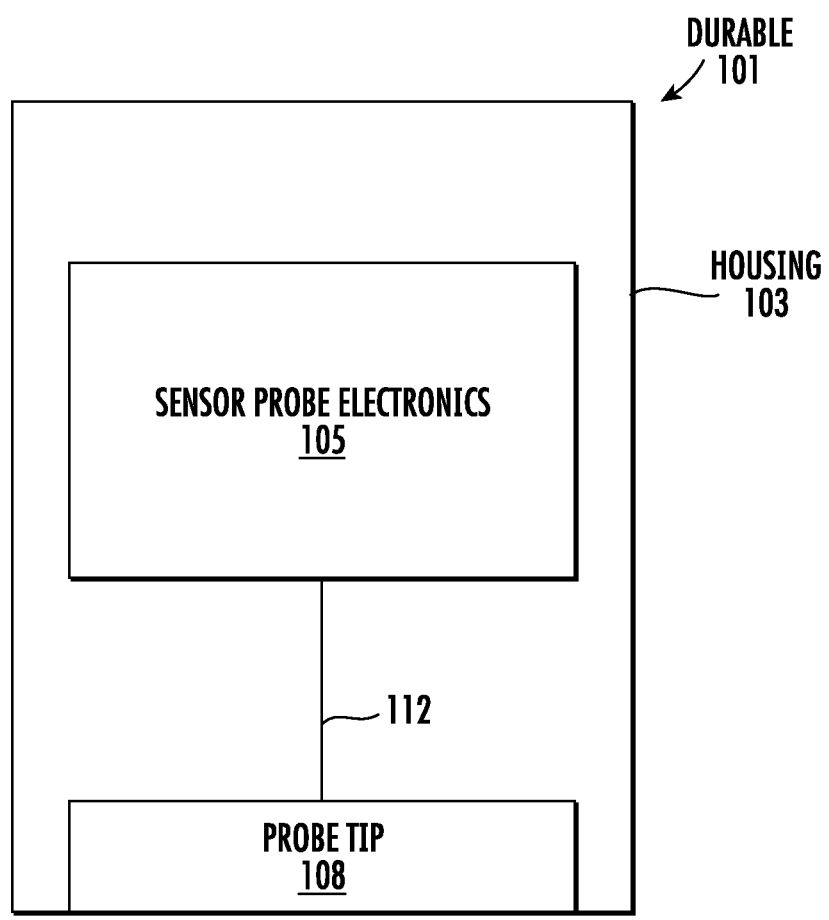
FIG. 1 shows a block diagram of a system unit for measuring various oximetry parameters of patient tissue.

Spectroscopy has been used for noninvasive measurements of various physiological properties in animal and human subjects. Visible (e.g., red light) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficients and the reduced scattering coefficients of the physiological medium by use of the photon diffusion approximation, Monte Carlo models, or other techniques. From the absorption coefficients at multiple wavelengths, concentrations of oxygenated and deoxygenated hemoglobins can be determined and from these concentrations, the tissue oxygen saturation can be calculated.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes of the index of refraction of the tissue and includes Mie scattering from larger structures such as mitochondria (the majority of tissue scattering is a result of mitochondria) and Rayleigh scattering from smaller structures such as intracellular vesicles. The absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations, and therefore oxygen saturation within the volume of the tissue probed. Further, the wavelengths of the light source or light sources and the relative positions of the light source(s) with respect to a single detector or multiple ones of the detectors, allow tissue oximetry measurements to be made for a predetermined tissue depth.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions.

Oximetry probes adapted for SRS and other spectroscopies can come into contact with tissue, other surfaces, fluids (both liquid and gas), or other elements that can contaminate the probes. An oximetry probe that contacts tissue, for example, can be contaminated by the tissue, bacteria on the tissue, viruses on the tissue, tissue fluid, debris on the tissue, the environment near the tissue, any one of these substances, other substances, or any combination of these substances. A sheath can shield an oximetry probe from contaminants, but the efficacy of a sheath can be compromised in a number of ways. The ways in which a sheath can be compromised, allowing an oximetry probe to be contaminated, can be known and unknown. For example, a sheath housing an oximetry device may open and allow contaminants to contact the oximetry probe. The sheath opening may be relatively small and not detectable by visual inspection and the small opening may allow contaminants to enter the sheath and contact the oximetry probe. The efficacy of a sheath can be compromised if the sheath has been previously used and the previous use is unknown. The efficacy of a sheath can also be compromised if the sheath is provided from an unknown source and the sterility or sanitation of the sheath is unknown. Either inside or outside surfaces of the sheath, or both, can be contaminated if the sheath is provided by an unknown source. If the previous use of a sheath is unknown and the sheath is reused, contaminants on the sheath from an initial use can be spread during subsequent use of the sheath. Sheaths and the oximetry probes in the sheath may be contaminated in a variety of other ways. Reuse of an oximetry probe after contamination may be precluded or may increase the cost of reuse due to the cost of sanitizing or sterilizing the oximetry probe. Oximetry probes and sheaths of the present invention are directed toward improved sanitation, sterilization, or both.

FIG. 1 shows a system unit 101 for measuring various parameters of tissue in a patient. System unit 101 is sometimes referred to as a durable system unit because the unit is reusable, such as when the unit is used in combination with a protective sheath. The parameters of the tissue measured by the system unit may include an oxygen saturation level (relative oxygen saturation, absolute oxygen saturation, or both), a total hemoglobin concentration, an oxygenated hemoglobin concentration, an deoxygenated hemoglobin concentration, blood flow, pulse rate, a signal level of light reflected from the tissue, melanin concentration of tissue, other tissue parameters, or any combination of the parameters. The system unit includes housing 103, sensor probe electronics 105, and a probe tip 108, which is connected to the sensor probe electronics via a wired connection 112. Connection 112 may be an electrical connection, an optical connection, or another wired connection including any number of wires (e.g., one, two, three, four, five, six, or more wires or optical fibers), or any combination of these or other types of connections. In other implementations, connection 112 may be a wireless connection, such as via a radio frequency (RF) or infrared (IR) connection.

Typically, the system unit is used by placing the probe tip in contact or close proximity to tissue (e.g., skin or internal organ or other tissue) at a site where tissue parameter measurements are desired. The system unit causes an input signal to be emitted by the probe tip into the tissue (e.g., human tissue). There may be multiple input signals, and these signals may have varying or different wavelengths of electromagnetic radiation. The input signal is transmitted into the tissue and reflected from the tissue, absorbed by the tissue, or transmitted through the tissue.

Then, after transmission through the tissue or reflection from the tissue, the signal is received at the probe tip. This received signal is received and analyzed by the sensor probe electronics. Based on the received signal, the sensor probe electronics determine various parameters of the tissue, such as an oxygen saturation level, a total hemoglobin concentration, an oxygenated hemoglobin concentration, an deoxygenated hemoglobin concentration, a blood flow, a pulse, a signal level of light reflected from the tissue, melanin concentration of tissue, or other tissue parameters. One or any combination of these parameters can be displayed on a display screen of the system unit.

In an implementation, the system unit is a tissue oximeter, which can measure oxygen saturation and hemoglobin concentration, without requiring a pulse or heartbeat. A tissue oximeter of the invention is applicable to many areas of medicine, surgery (including plastic surgery and spinal surgery), post-surgery, athlete monitoring, and other uses. The tissue oximeter can make oxygen saturation and hemoglobin concentration measurements of tissue where there is no pulse, such as tissue that has been separated from the body (e.g., a tissue flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. There are various implementations of systems and techniques for measuring oxygen saturation, such as discussed in U.S. patent applications 62/959,757, 62/959,764, 62/959,778, 62/959,787, and 62/959,795, filed Jan. 10, 2020; Ser. No. 17/146,176, 17/146,182, 17/146,186, 17/146,190, 17/146,194, and 17/146,201, filed Jan. 11, 2021; and Ser. No. 29/720,112, 29/720,115, 29/720,120, and 29/720,122, filed Jan. 9, 2020. These patent applications are incorporated by reference along with all other references cited in these applications.

Figure 2:
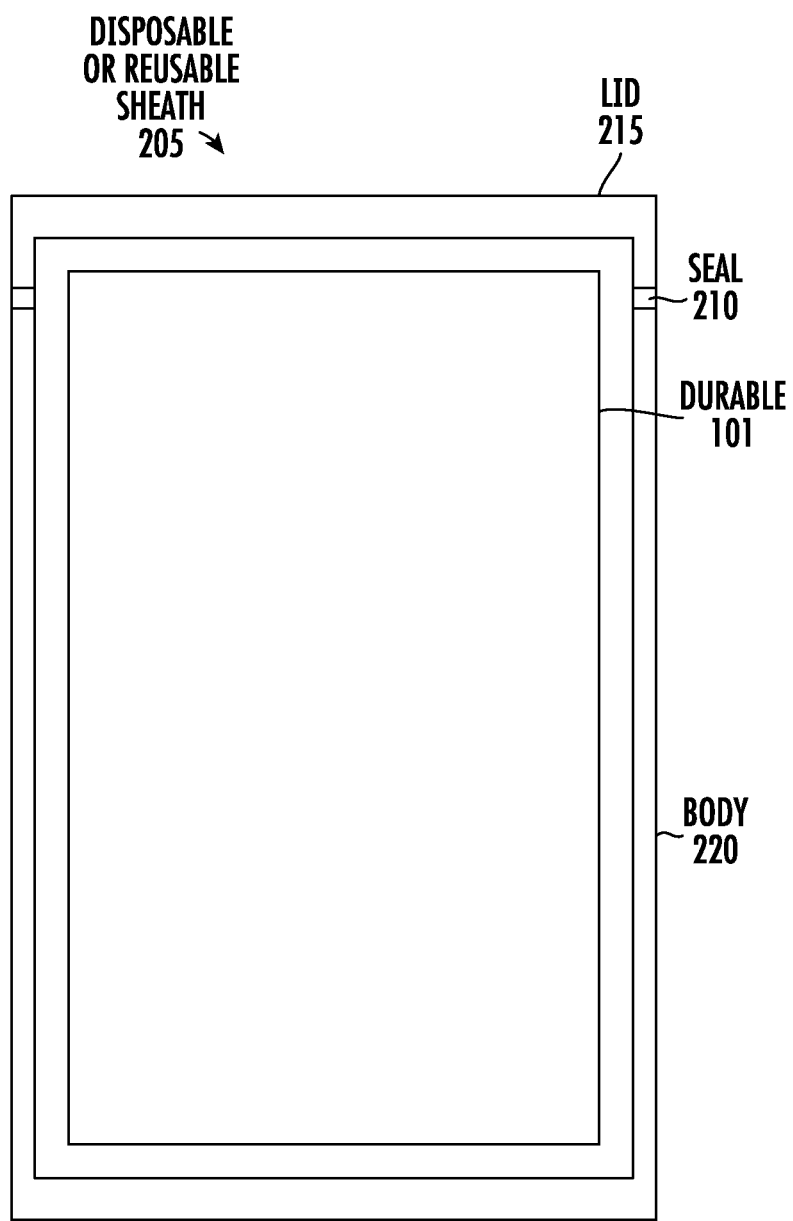
FIG. 2 shows a block diagram of the system unit housed in a sheath.

FIG. 2 shows system unit 101 housed in a sheath 205. The sheath includes a lid 215 and a body 220, which may be sealed to the lid via a seal 210. The lid may be separable from the body or may be connected to the body, such as via a hinge. The hinge may allow the lid to rotate to seal the lid to the body. The sheath may be a disposable sheath or a sheath that is reusable. For example, the system unit and sheath may travel with a patient from surgery (e.g., use) to post-surgery (e.g., reuse) for tissue monitoring.

With the lid opened, the system unit may be inserted into the sheath, and thereafter the lid may be sealed to the body to house and seal the system unit in the sheath. The system unit may then be used to make tissue parameter measurements in the sealed environment provided by the sheath. The sheath can protect the system unit from contacting elements that the sheath contacts, such as tissue, tissue fluid, biological agents (e.g., bacteria, viruses, prions, and pyrogens), debris, and other contaminants. When the lid is open and the seal is broken, the system unit may be removed from the sheath. Because the system unit is sealed into the sheath by the body, lid, and seal, the system unit can remain relatively clean, sanitized, or sterile for reuse.

Figure 3:
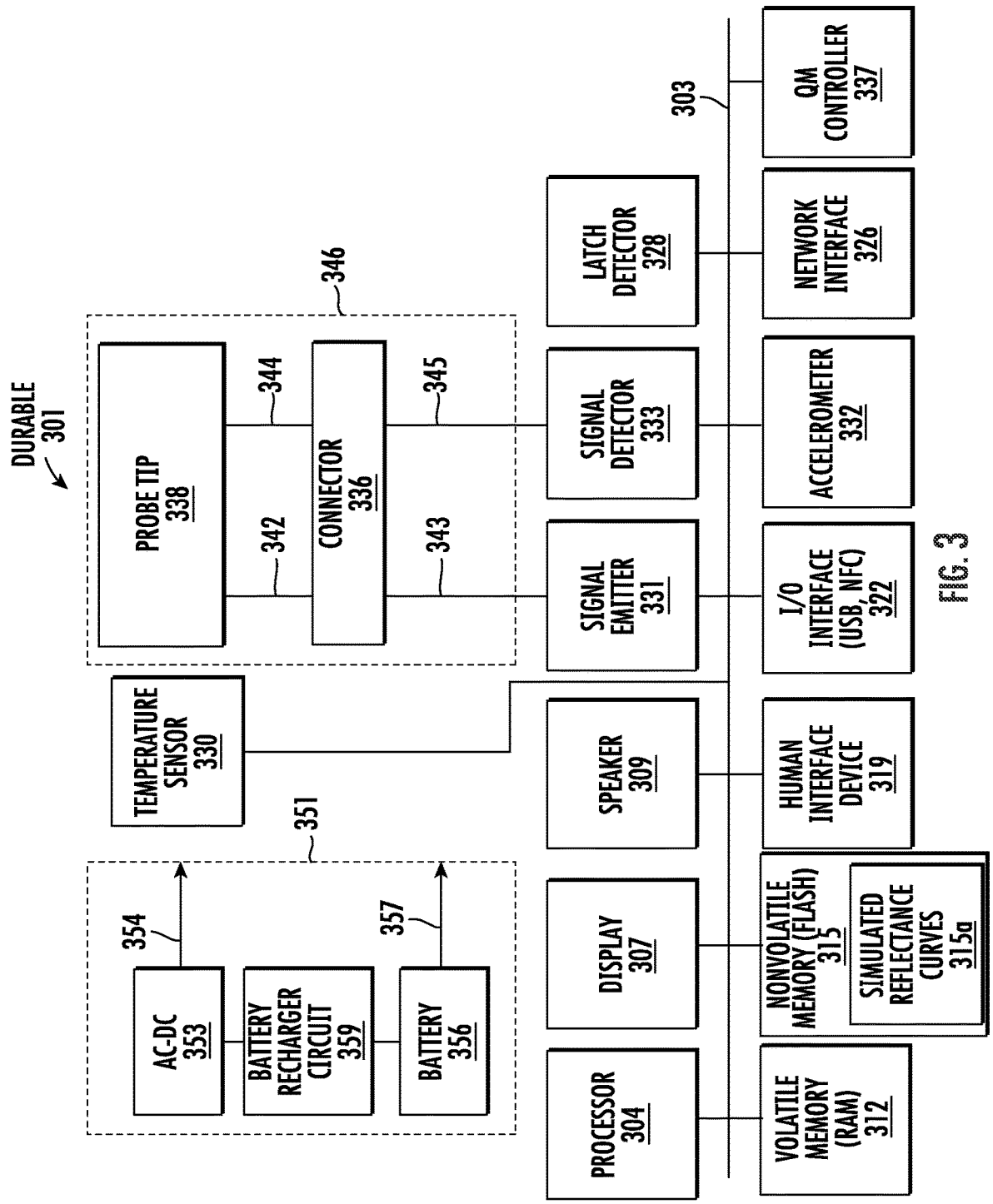
FIG. 3 shows a block diagram of the system unit, in an implementation.

FIG. 3 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, accelerometer 332, and a quality metric controller 337. These components are housed within housing 103. Different implementations of the system may include any number of the components described, in any combination or configuration, and may also include other components not shown.

The components are linked together via a bus 303, which represents the system bus architecture of the system unit. Although FIG. 3 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or other port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., a fiber optic cable), a number of waveguides (e.g., a number of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, or both. In this implementation, the signal emitters and signal detectors may be electrical emitters and detectors that control light emitters, light detectors, or both in the probe tip.

In an implementation, where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, signal emitter 331 includes one or more light sources that emit light at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs).

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a standby mode signal and may place the system unit in a standby power mode (a lower power mode than a normal operation mode where oximetry measurements can be made by the system unit), or a power-down signal and may power down the system unit.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue.

The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

In an implementation, the latch detector 328 is adapted to detect whether a latch of the sheath is latched or unlatched. If the latch is latched, then the system unit is housed and enclosed in the sheath. In this configuration, with the system unit housed and enclosed in the sheath, the system unit may not be contaminated by material contacting the outside surface of the sheath. If the latch is unlatched and the system unit is in the sheath, then the system unit might be contaminated with material contacting the outside surface of the sheath. That is, the seal that seals the lid of the sheath to the body of the sheath may be unsealed (i.e., opened) and contaminates may pass from outside of the sheath to the inside of the sheath where the system unit is located.

In an implementation, at least a first portion of the latch is metal. Other portions of the latch may be metal or other material, such as a plastic material. The first portion of the latch is a first distance from the latch detector when the latch is latched and is a second distance from the latch detector when the latch is unlatched. The first distance is less than the second distance.

In an implementation, the latch detector includes an inductor that can inductively couple to the first portion of the latch. The inductor can be driven with a direct current or an alternating current and thus detect when the first portion of the latch moves toward the latch detector or away from the latch detector. The latch detector can be calibrated so that the latch detector can detect when the latch moves to the first distance away from the latch detector or farther than the first distance away from the latch detector. The latch detector can include an analog-to-digital converter, a digital signal processor (DSP), or both that digitize and analyze the current flowing through the inductor. One or both of these circuits can communicate the digitalized information to the processor that can determine whether the latch is open or closed. The processor can display a message on the display to indicate whether the latch is open or closed, whether the seal for the sheath is sealed or unsealed, warn of potential contamination, or other messages associated with the latch being opened or closed.

In an embodiment, the latch detector is a capacitive detector that can capacitively couple to the latch. The capacitive detector can detect the latch in the latched position at a first distance from the capacitive detector and moving away from the latched position and the first distance.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, MATLAB (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses the system unit of the invention through a network such as the Internet. The user will be able to see the data being gathered by the system unit. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
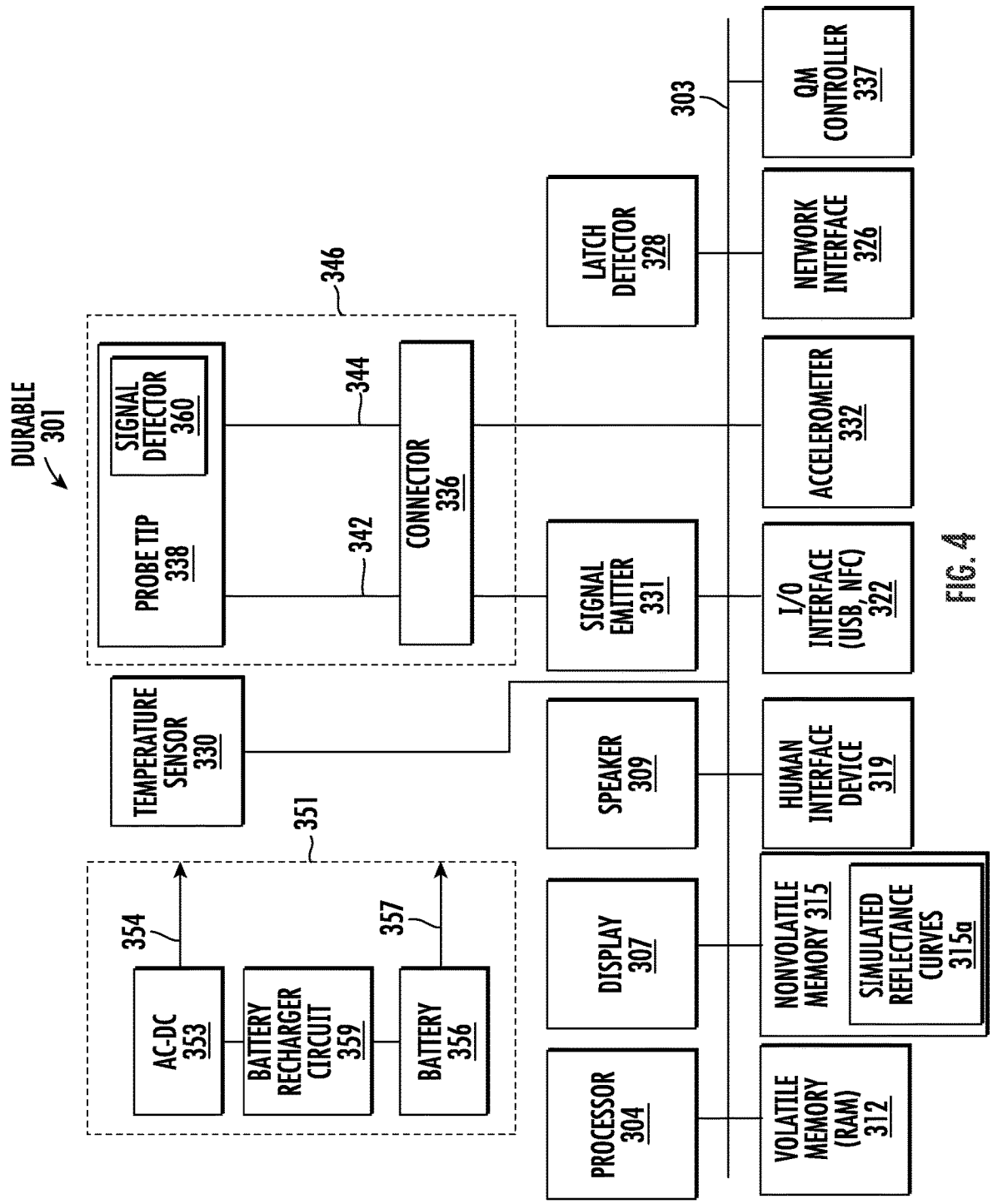
FIG. 4 shows a block diagram of the system unit, in an implementation.

FIG. 4 shows a block diagram of system unit 401, in an implementation. System unit 401 is similar to system unit 301 but differs in that the signal detector 344 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 5:
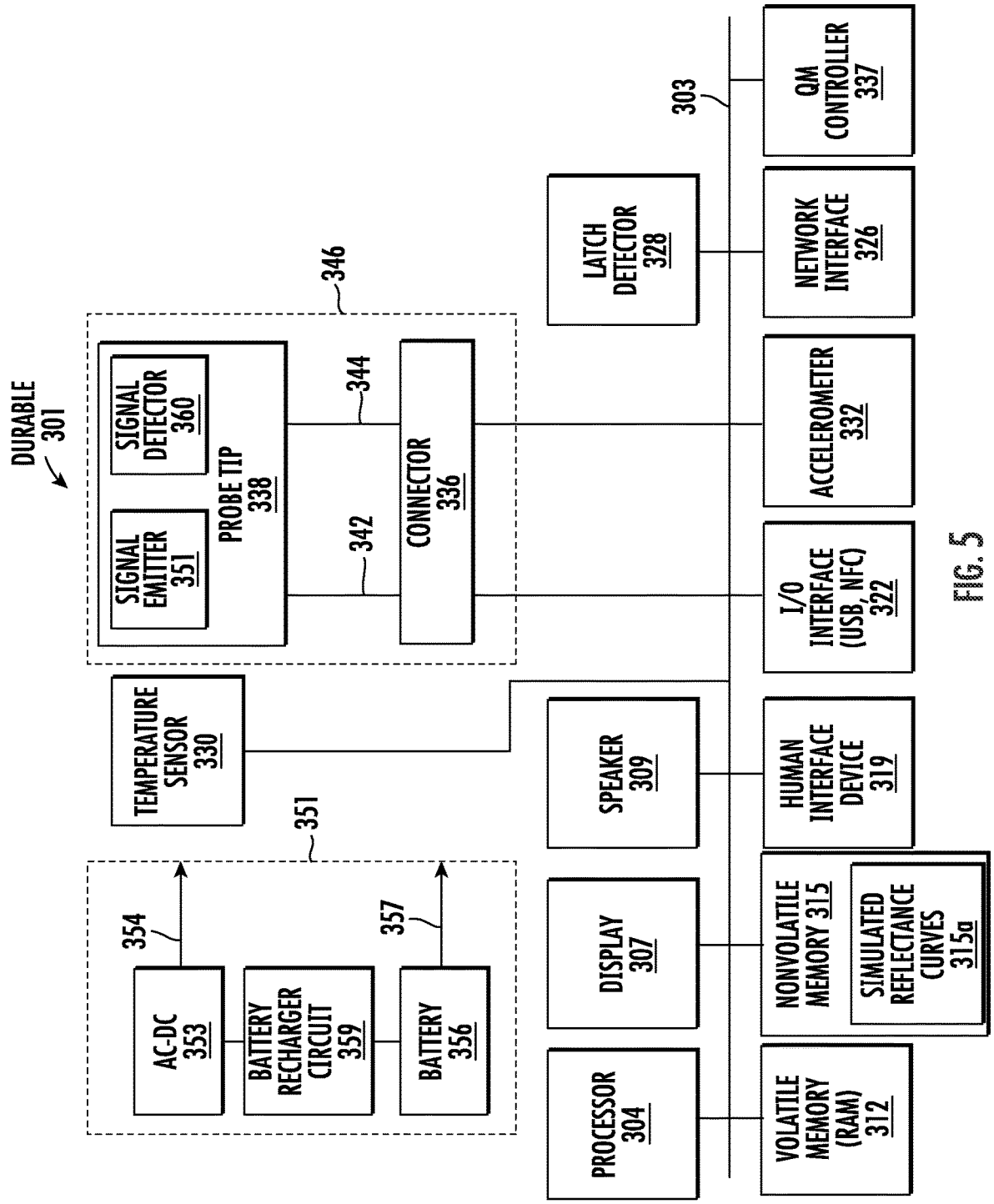
FIG. 5 shows a block diagram of the system unit, in an implementation.

FIG. 5 shows a block diagram of system unit 501, in an implementation. System unit 501 is similar to system units 301 and 401 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector.

Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system is battery operated. The DC output of a battery 356 is connected (indicated by an arrow 357) to the components of the system unit needing power. The battery may be recharged via a recharger circuit 359, which received DC power from the AC-to-DC converter. The AC-to-DC converter and recharger circuit may be combined into a single circuit. In an implementation, the battery is rechargeable via magnetic charging or induction charging.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 6:
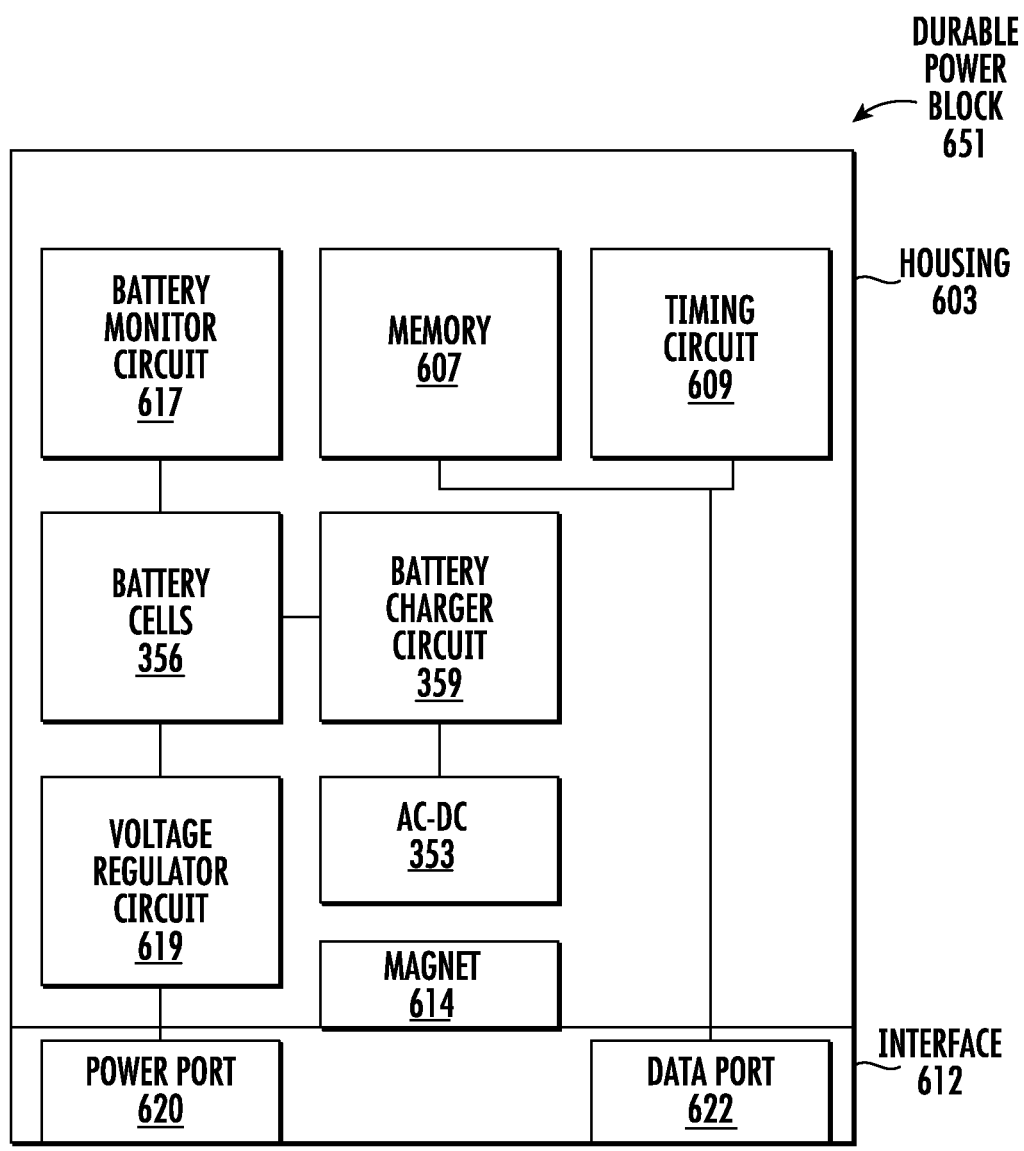
FIG. 6 shows the power block, in an implementation.

FIG. 6 shows block 651 that is a power block, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage, elapsed usage time, or any combination of these elements. In an implementation, if the identifier is not a known identifier that is known to the system unit, then the processor with not allow the system unit to operate with the power block. That is, the system unit will not operate with a power block manufactured by an unknown manufacturer. Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Also, using a known battery from a known manufacturer provides that the stem unit will operate for a known period of time so that the system unit will not run out of battery power during a medical procedure, such as a surgery. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements without displaying information on the display about the authenticity or the inauthenticity of the power block.

In an implementation, the memory of the power block stores an indicator that indicates whether the battery has been previously used. The indicator may be the time information for the amount of time that the power block has operated. A nonzero use time stored in the memory is an indicator that the power block has been previously used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that retrieved the system unit from the power block's memory, then the system unit will not operate with the power block. The implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts (e.g., a data line and a shared ground contact with the power port). The electrical contacts are arranged in an arrangement, such as in a row, in a square, in a rectangle, another arrangement. The system unit includes a power port that includes at least two electrical contacts (e.g., a power contact and a ground contact) and includes a data port that includes at least two electrical contacts (e.g., a data line and a shared ground contact with the power port). The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

Figure 7:
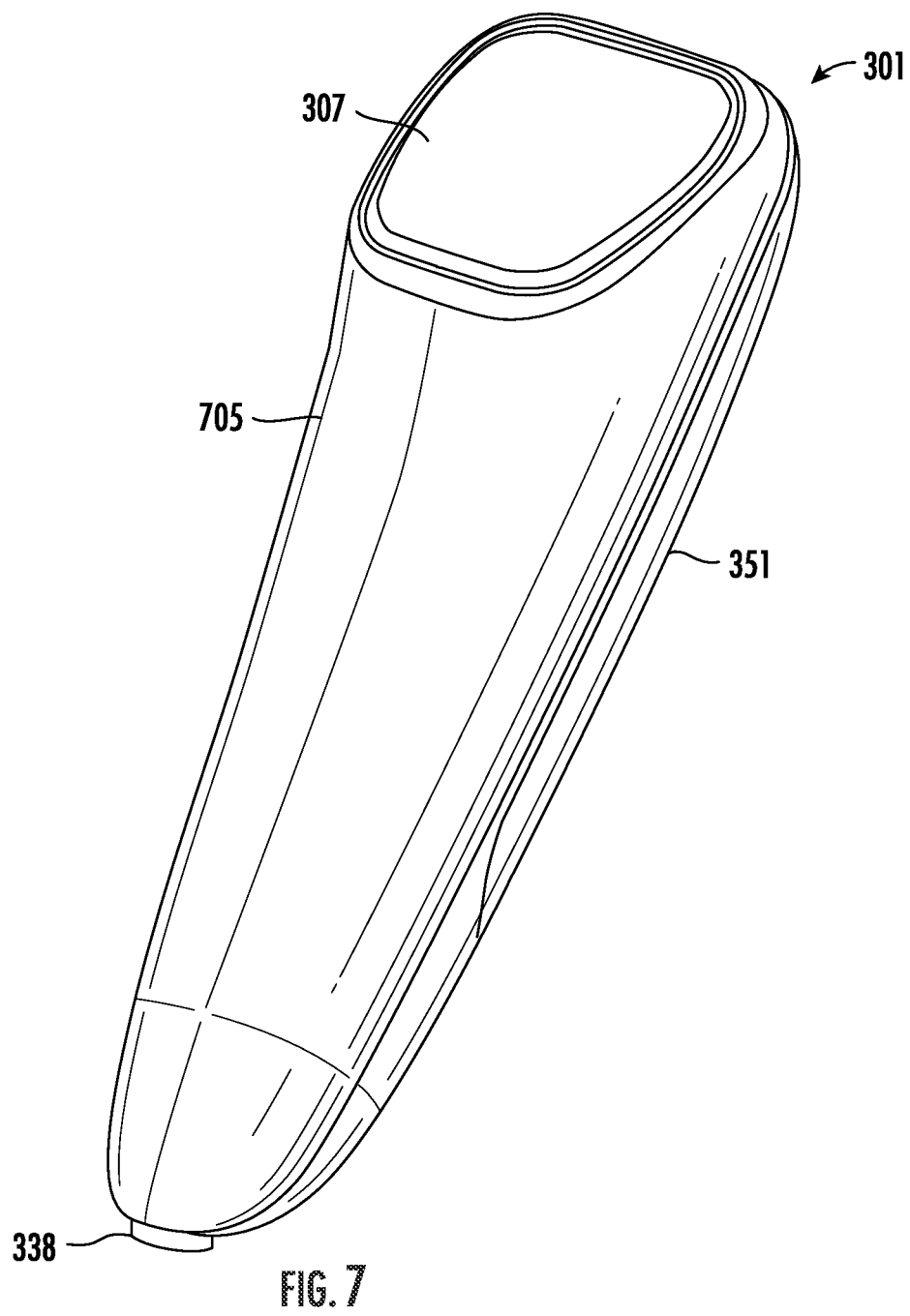
FIG. 7 shows a perspective view of the system unit and power block coupled to the system unit, in an implementation.

FIG. 7 shows a perspective view of the system unit 301 and power block 351 coupled to the system unit, in an implementation. The display 307 of the system unit is located at a first end of the system unit and the probe tip 338 is located at a second end of the system unit where the first and second ends of proximal and distal ends of the unit. The housing of the system unit tapers from the first end to the second end. The described circuit elements are housed in the housing 705 of the system unit. housing 705 of the system unit. When the second window of the sheath is in contact with tissue, the first window of the sheath and the display of the system unit faces away from the tissue for easy visibility of the display. In an implementation where the system unit is used without a sheath, when the probe face of the system unit is in contact with tissue, the display faces away from the tissue for easy visibility of the display.

Figure 8:
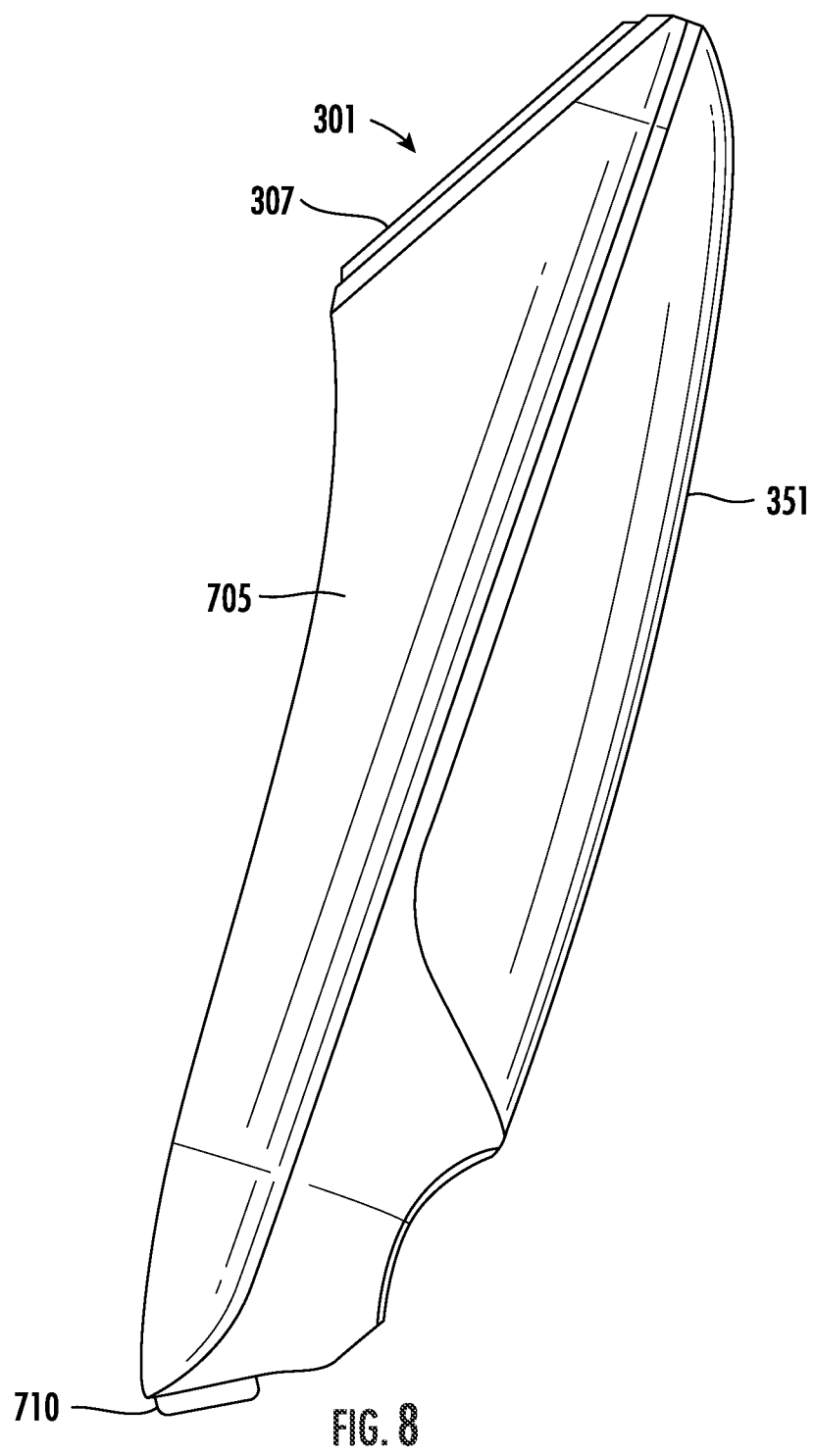
FIG. 8 shows a side view of the system unit, in an implementation.

FIG. 8 shows a side view system unit 301, in an implementation. The housing 705 of the system unit includes a bezel 710 that houses a portion of the probe tip. The bezel includes an opening the exposes a probe face of the probe tip.

Figure 9:
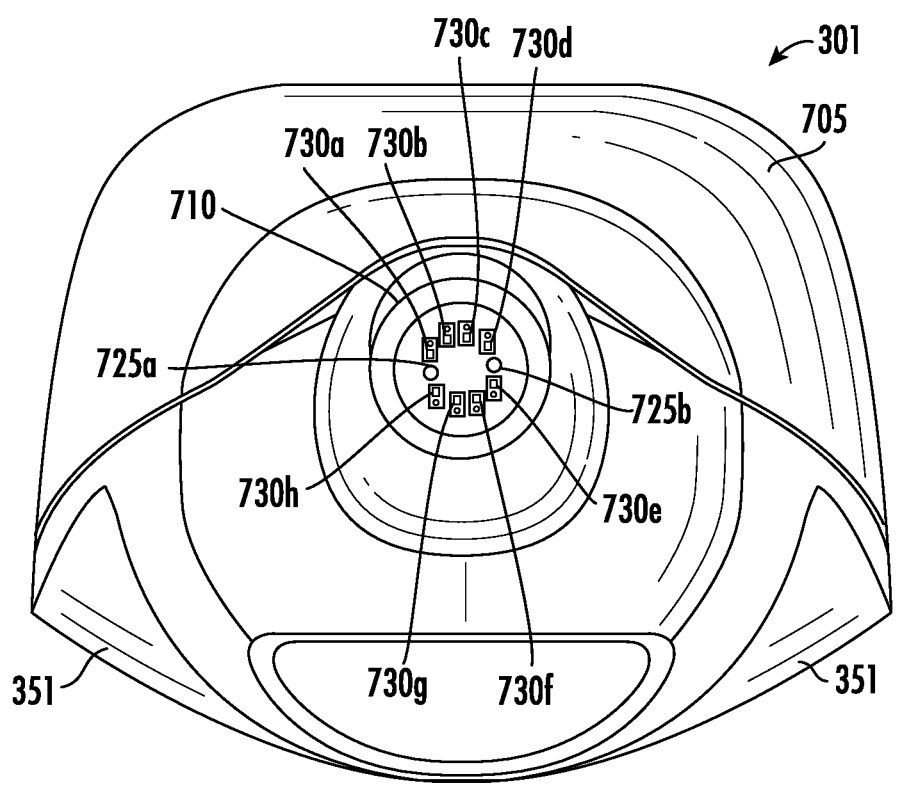
FIG. 9 shows an end view of the second end of the system unit, in an implementation.

FIG. 9 shows an end view of the second end of the system unit, in an implementation. The end of bezel 710 is shown with the probe face 715 in the opening of the bezel. The probe face may include an aperture plate 720 that includes a number of source apertures, for example, source apertures 725a and 725b, and includes a number of detector apertures 730a-730h. Each of the source apertures may be included in a source structure that may include light sources, such as one or more of optical fibers, laser diodes, LEDs, one or more portions of the aperture plate, or other structures at the probe tip in any combination. Each of the detector apertures may be included in a detector structure that may include light detectors, such as one or more of optical fibers, photodetectors, one or more portions of the aperture plate, or other structures at the probe tip in any combination.

Figure 10A:
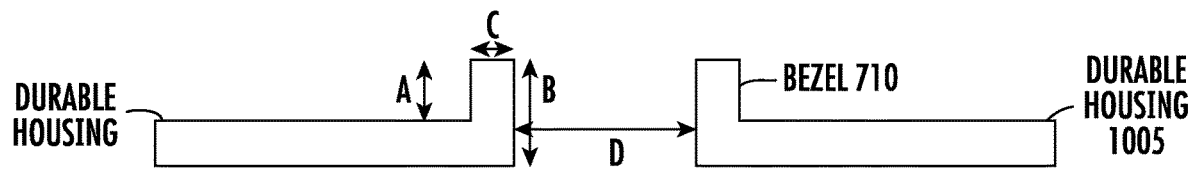
FIGS. 10A-10D show a number of steps for forming the probe face of the probe tip and forming the finished bezel of the housing of the system unit.

FIGS. 10A-10D show a number of steps for forming the probe face 715 of the probe tip 338 and forming the finished bezel 710 of the housing 1005 of the system unit 301. FIG. 10a shows the bezel 710 of the housing 1005 at an initial height A where the height is from the outside surface of the housing to the top of the bezel. Height A may be from about 3.5 millimeters to about 4 millimeters. In a specific implementation, height A is about 3.75 millimeters. The inner height B of the bezel is from the inside surface of the housing to the top of the bezel. Height B may be from about 4.5 millimeters to about 5.5 millimeters. In a specific implementation, height B is about 5.05 millimeters. The diameter D of the opening of the bezel may be from about 8 millimeters to about 10 millimeters. In a specific implementation, the diameter of the opening of the bezel may be about 9.1 millimeters. The width C of the bezel at the bezel's end may be about 1.0 millimeters to about 2.0 millimeters. The width C may vary around the circumference of the bezel. In a specific implementation, the width C of the bezel is about 1.5 millimeters.

Figure 10B:
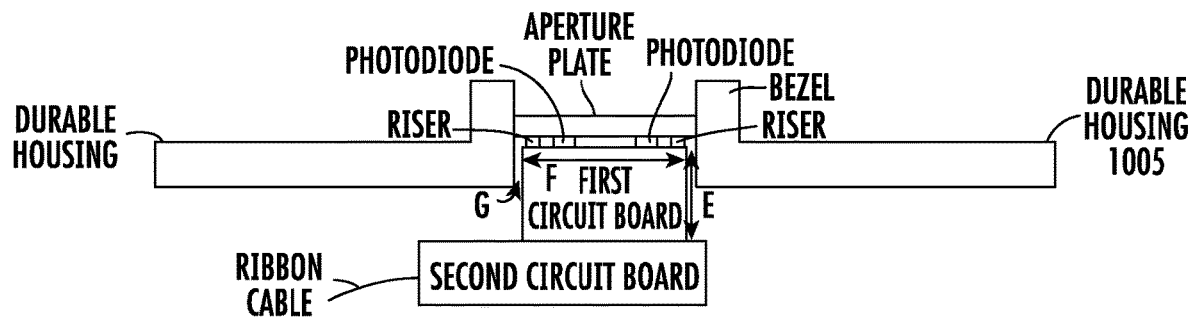

FIG. 10B shows the housing and bezel with a portion of the probe tip 338 in the housing and bezel. The portion of the probe tip shown includes a first circuit board 1020, a second circuit board 1025, riser 1030, photodiodes 1035, an aperture plate 1040, and a ribbon cable 1045 connected to the second circuit board. The first and second circuit boards may include electrical traces that are coupled. The second circuit board may be a fiberglass circuit board (e.g., FR4) that includes electrical traces that are connected to electrical traces of the first circuit board. The electrical traces of the first circuit board may extend upward from the second circuit board along the outer surface of the first circuit board. The first and second circuit boards may be connected by mechanical fasters, plastic welding, an adhesive (e.g., epoxy), another material, or any combination of these materials. The first circuit board may have a diameter F of about 6 millimeters to about 8 millimeters. In a specific implementation, the diameter F of the first circuit board is about 7 millimeters. The first circuit board may have a height E of about 3 millimeters to about 4 millimeters. In a specific implementation, the height E of the first circuit board is about 3.5 millimeters.

A distance G between the side of the first circuit board and the inner sidewall of the bezel may be about 0.5 millimeters to about 1.5 millimeters. In a specific embodiment, the distance between the side of the first circuit board and the inner sidewall of the bezel may be about 1.05 millimeters.

The riser may be connected to both the first circuit board and the aperture plate and may separate the first circuit board and aperture plate may be predetermined height. The photodiodes may be mounted on a top surface of the first circuit board and be connected to the electrical traces of the first circuit board. The aperture plate may include an aperture for each photodiode that is mounted on the first surface of the first circuit board and the diodes may respectively be inside the apertures. The height of each riser may be about 100 micrometers to about 200 micrometers. In an implementation, the height of each riser is about 150 micrometers.

Figure 10C:
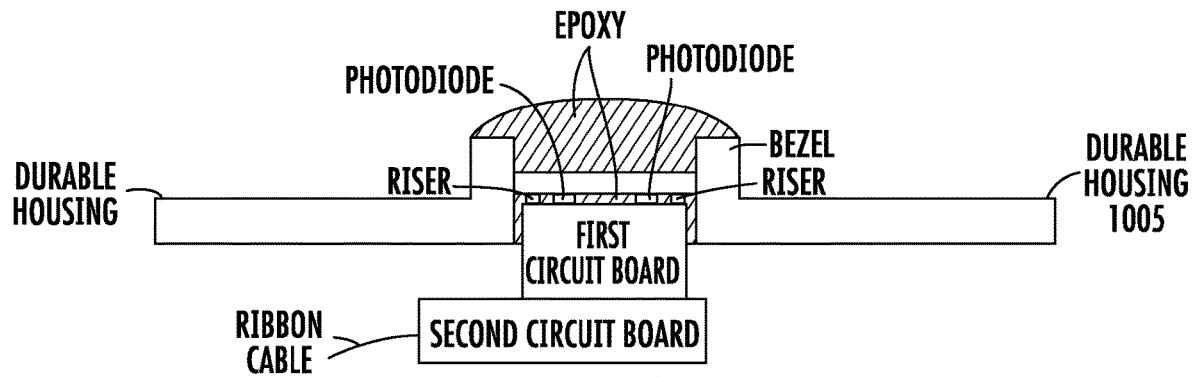

After the portion of the probe tip shown in FIG. 10B is placed into the opening of the bezel, epoxy is flowed into the opening as shown in FIG. 10C. The epoxy may flow into the apertures of the aperture plate, along the sides of the first circuit board, and may flow to the second circuit board and around the sides of the second circuit board.

Figure 10D:
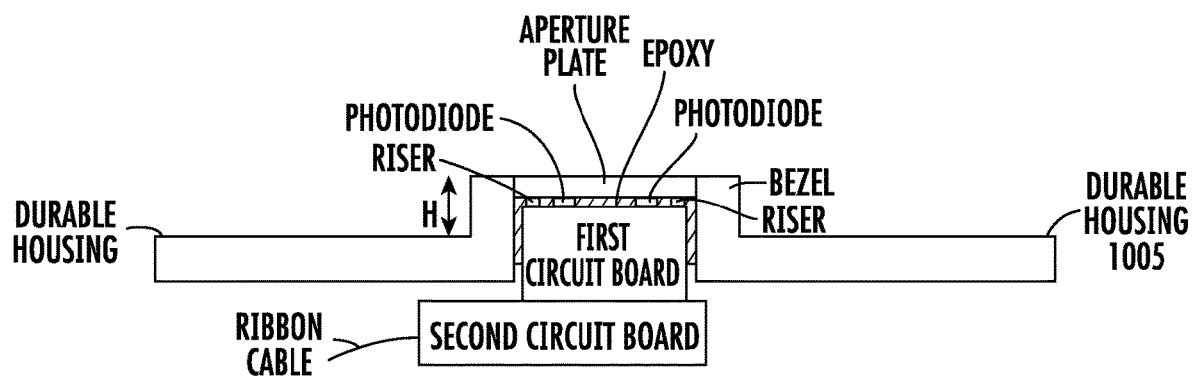

After the epoxy cures, the epoxy and a portion of the side of the bezel may be removed (e.g., polished down) to a final height, as shown in FIG. 10D. The final outside height H of the bezel may be about 2.0 millimeters to about 3 millimeters. In a specific implementation, the final outside height H of the bezel is about 2.58 millimeters. In an implementation, a portion of the aperture plate may also be thinned (e.g., polished thinner) when the bezel and epoxy are removed. The aperture plate can include a marker embedded in the plate. The embedded marker is exposed and polished away in the polishing process, the polishing is completed when the marker is polished away.

In an implementation, the epoxy is polished down to the surface of the tops of the photodetectors inside the apertures of the aperture plate. In another implementation, a thin layer of epoxy remains over the tops of the photodiodes after polishing.

Figure 11:
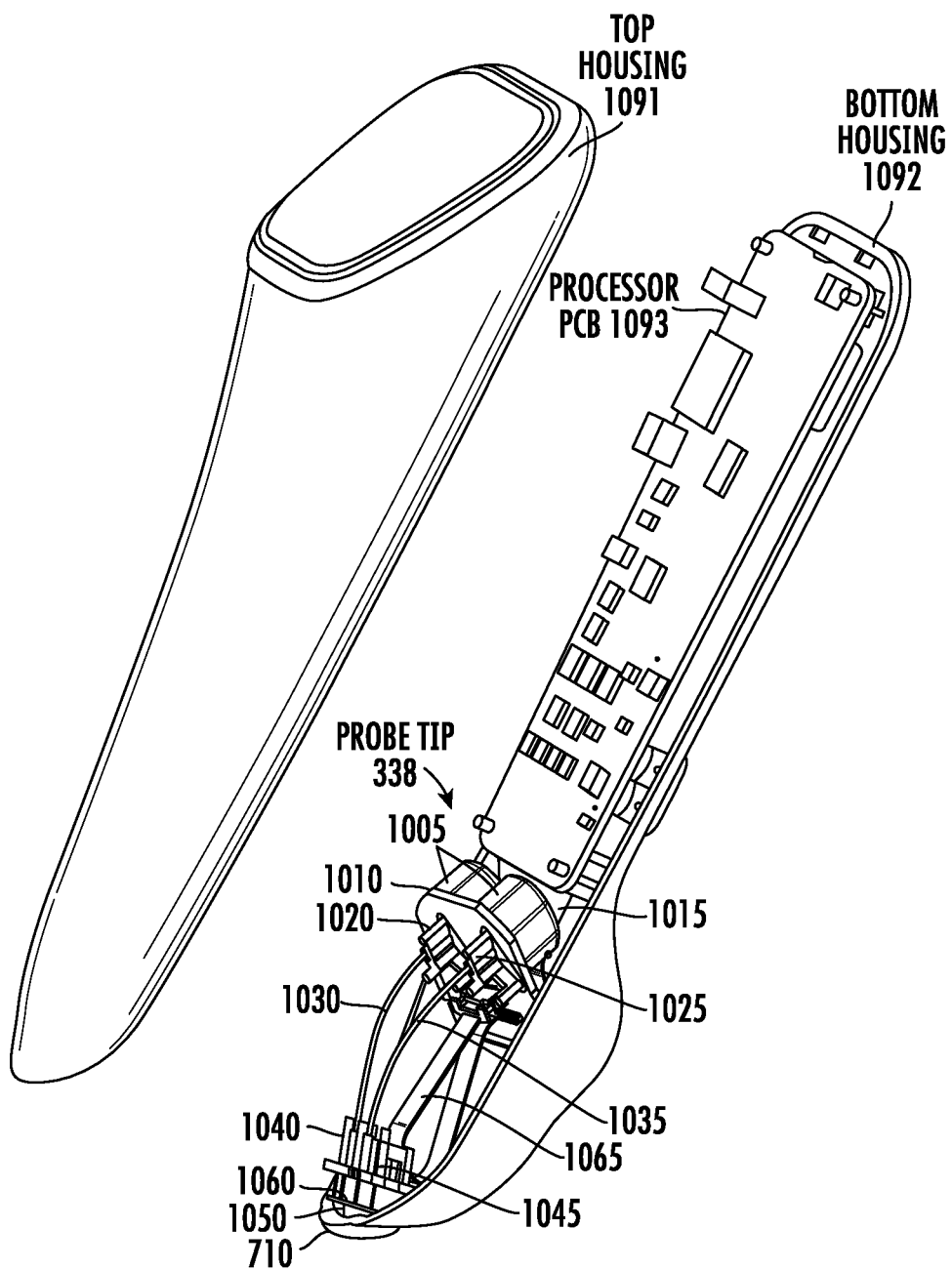
FIG. 11 shows a view of the system unit with a top housing of the system unit separated from a bottom housing of the system unit.

FIG. 11 shows a view of the system unit with a top housing 1091 of the system unit separated from a bottom housing 1092 of the system unit. This figure shows a PCB 1093 on which various circuits of the system unit are mounted, such as the processor 304, volatile memory 312, nonvolatile memory 315, human interface device (HID) 319, input-output (I/O) interface 322, network interface 326, and accelerometer 332.

The probe tip 338 is attached to a lower portion of the bottom housing. The probe tip includes two reflector domes 1005, an LED PCB 1010, a first optical fiber holder 1020, a second optical fiber holder 1025, a third optical fiber holder 1040, a fourth optical fiber holder 1045, a first optical fiber 1030, a second optical fiber 1035, a first PCB 1050, a second PCB 1060, a first ribbon cable 1015, and a second ribbon cable 1065.

Figure 12:
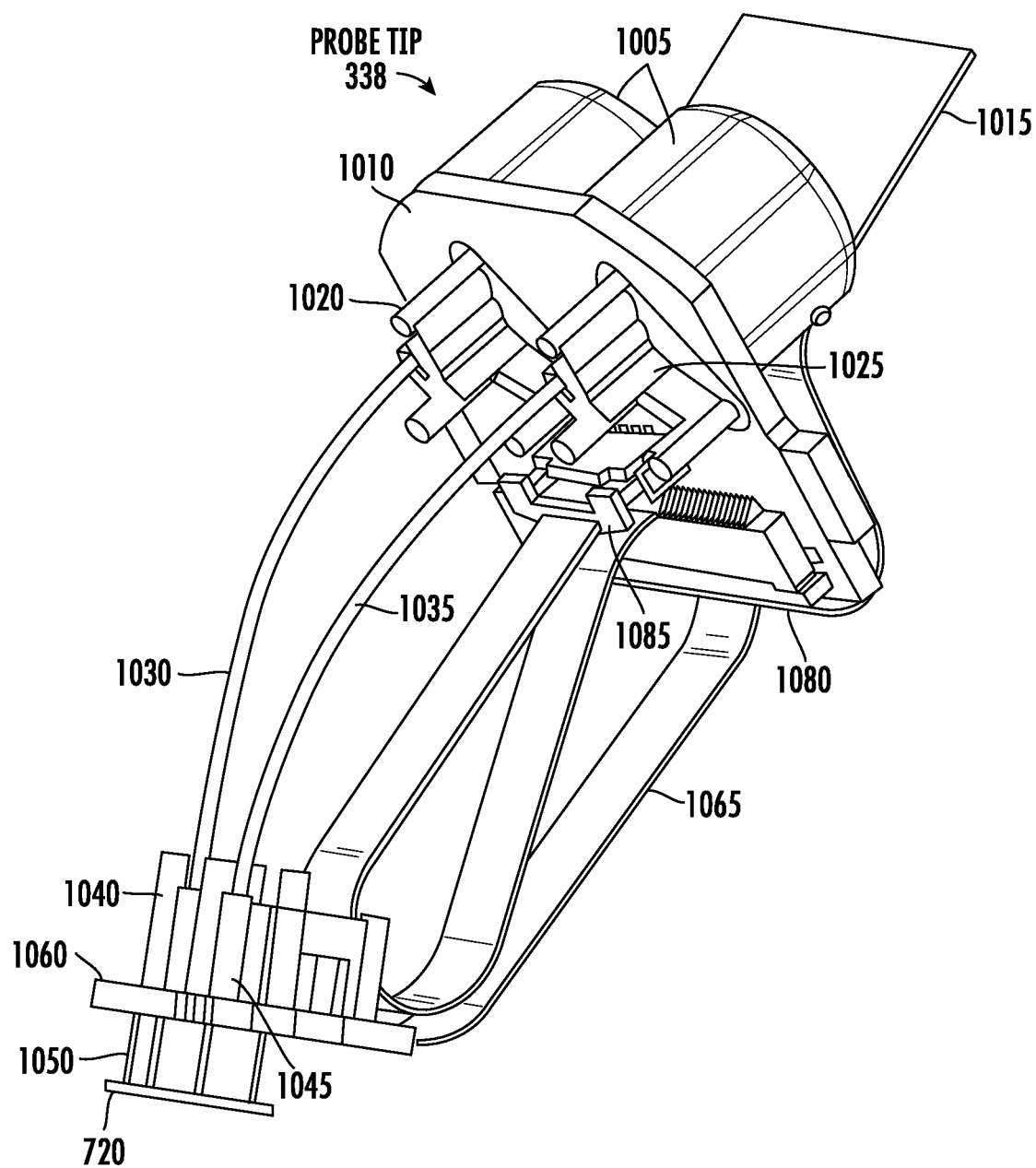
FIG. 12 shows the probe tip separate from the housing of the system unit and shows additional elements of the probe tip.

FIG. 12 shows the probe tip separate from the housing of the system unit and shows additional elements of the probe tip. As shown in this figure, the probe tip additionally includes an aperture plate 720, a first electrical connector 1080, and a second electrical connector 1085.

Figure 13:
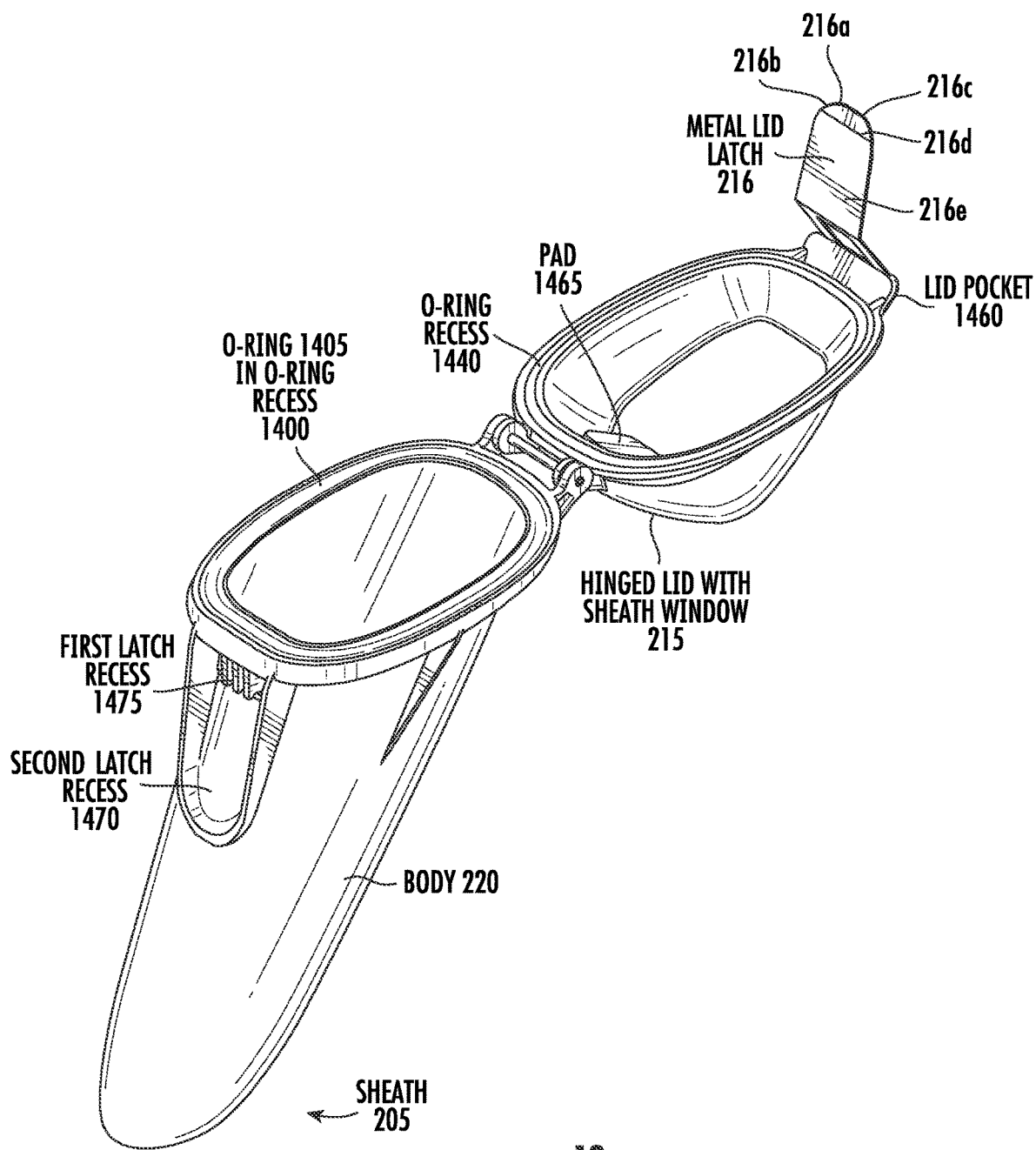
FIG. 13 shows a perspective view of the sheath, in an implementation.

FIG. 13 shows a perspective view of the sheath 205, in an implementation. The lid 215 is shown in an open position with respect to the body 220 where a system unit can be inserted into the sheath or removed from the sheath. The hinge that connects the lid and the body can be on a backside of the sheath. The body can include an o-ring recess 1400 of the top of the body. An o-ring 1405 is shown in the recess. The lid can also include an o-ring recess 4110 on the bottom of the lid. The o-ring recesses of the body and lid can contact the o-ring when the lid is closed against the body. The o-ring can form a seal that seals the lib to the body so that contaminants cannot enter the seal between the lid and body.

The latch can have a rounded end 216a and rounded corners 216b at the end of the latch. The end, corners, and edges of the latch can be relatively smooth. The smooth surface will not tear surgical gloves when the sheath and system unit are used.

Figure 14:
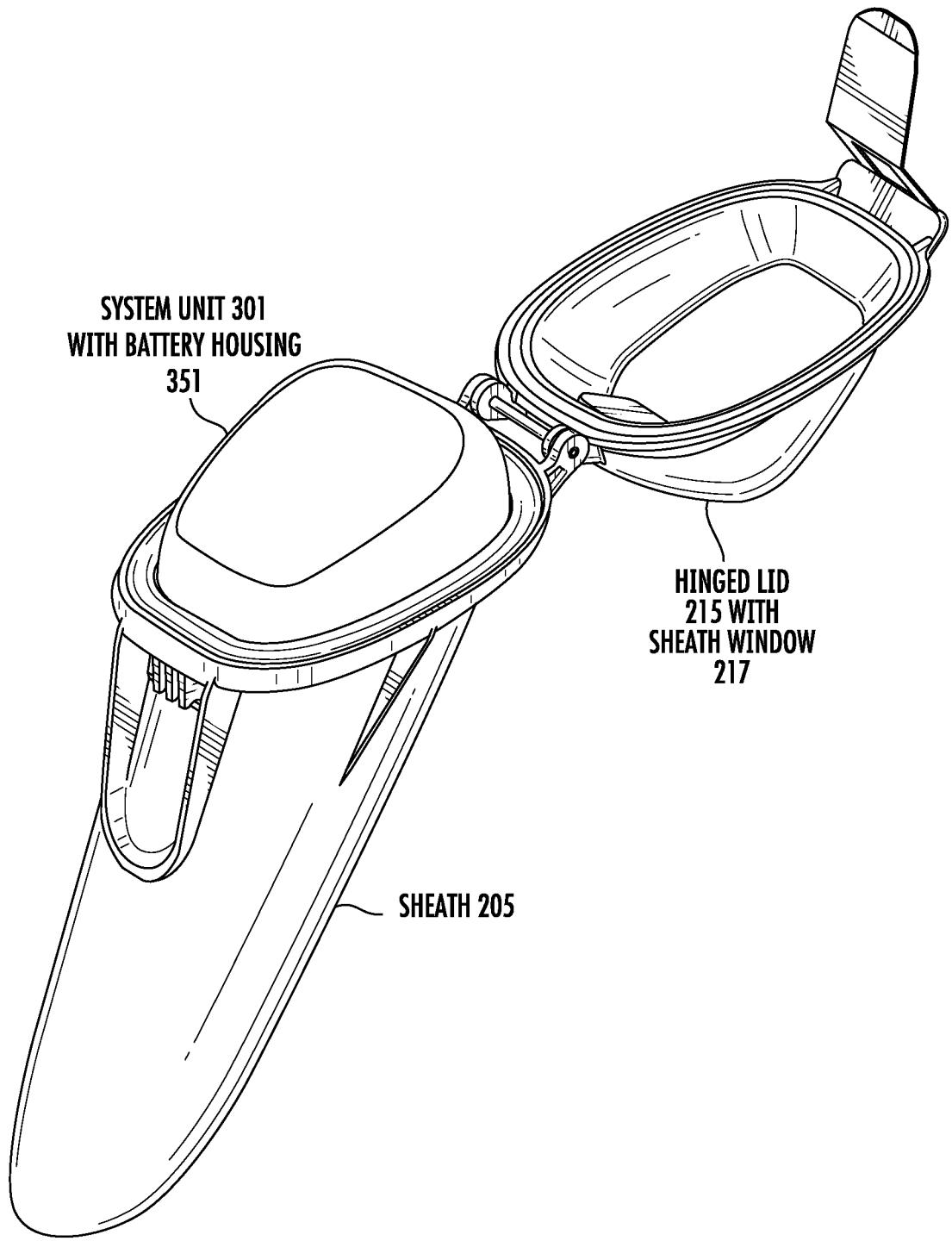
FIG. 14 shows a perspective view of the sheath, system unit, and power block, in an implementation.

FIG. 14 shows a perspective view of the sheath, system unit, and power block, in an implementation. The sheath is shown with the sheath lid open and the system unit with the power block attached is in the sheath. The probe face of the system unit may be in contact with the second window of the sheath.

Figure 15:
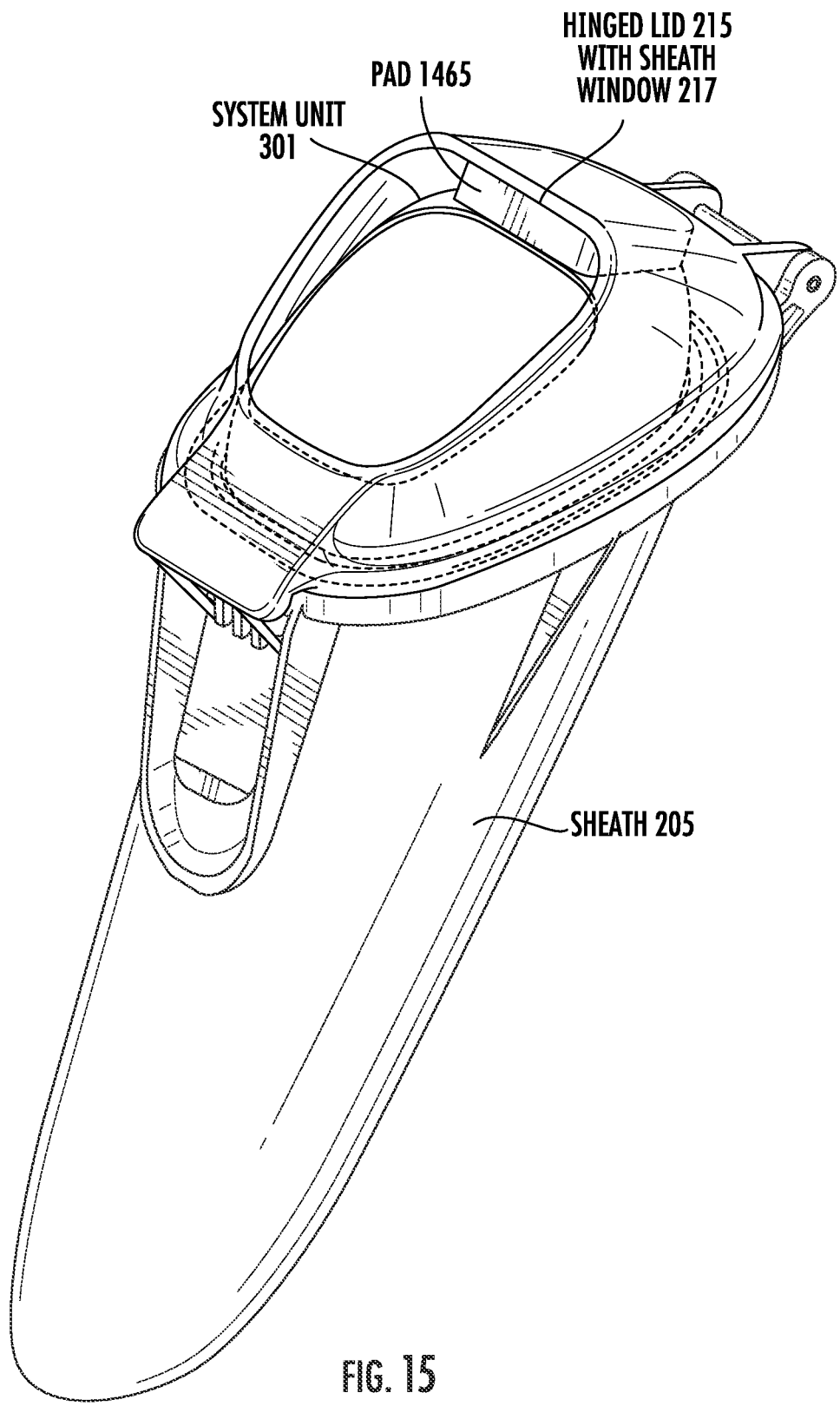
FIG. 15 shows a perspective view of the sheath, system unit, and power block, in an implementation.
Figure 17:
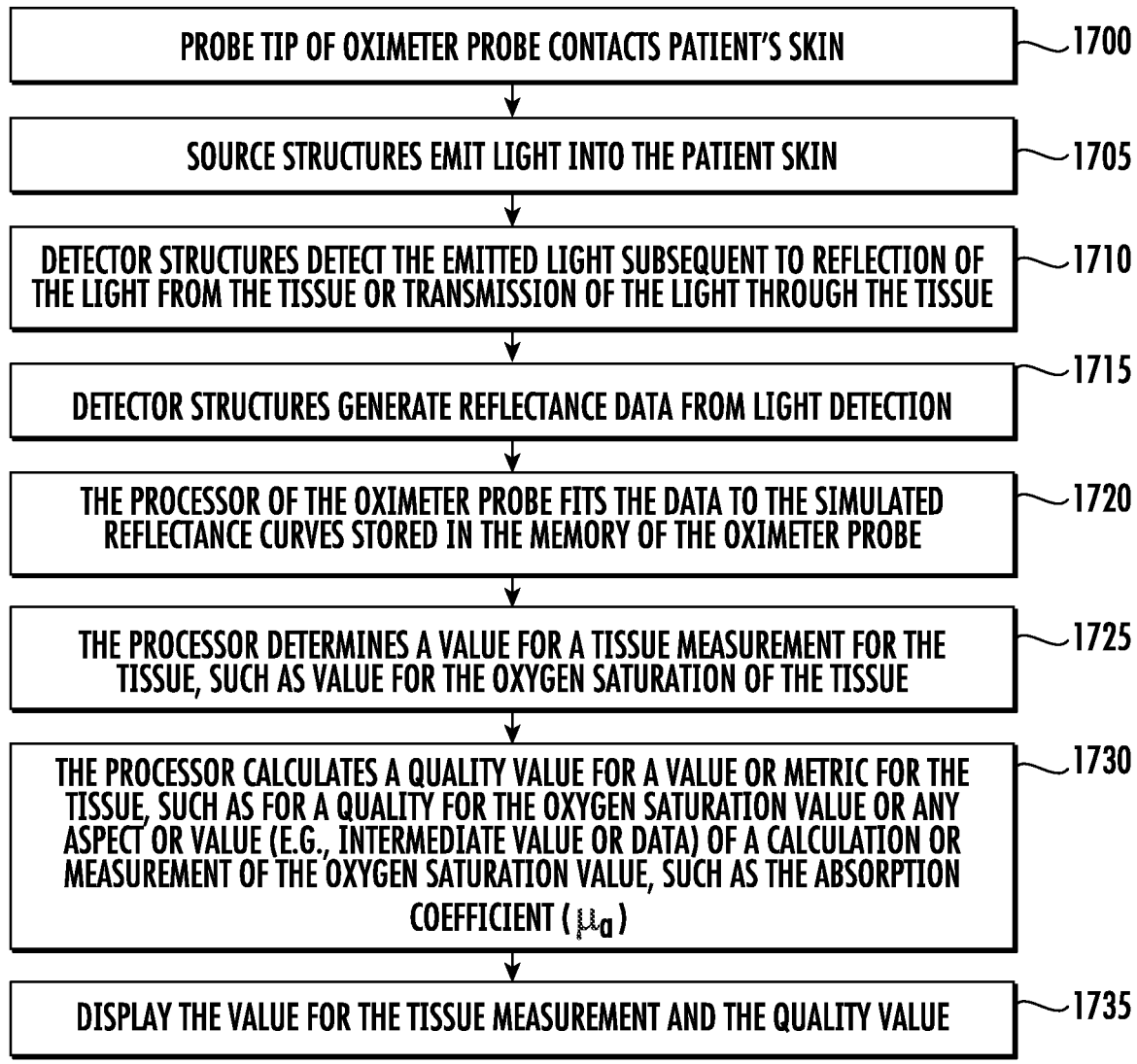
FIG. 17 shows a flow diagram of a method for determining and displaying a quality value on the system unit in an implementation.

FIG. 15 shows a perspective view of the sheath, system unit, and power block, in an implementation. The sheath is shown in FIG. 17 with the lid 215 closed against the body 220 of the sheath and with the latch in a latched position against the body. The lid may be formed of a first plastic material that can be transparent (e.g., the window of the lid), translucent (e.g., portions of the lid attached to the window), opaque, or any combination of these properties. The body may be formed of a second plastic that can be transparent, translucent, opaque, or any combination of these properties. The second window of the body may be attached to the body via an adhesive (e.g., epoxy), plastic weld, or other fasteners. The second widow may form a seal with the body where the second window attaches to the body where contaminants cannot pass through the seal to contaminate a system unit in the sheath via the seal.

The display of the system unit is visible through the first window of the lid of the sheath. Information (e.g., text, graphics, or both) that is displayed on the display of the system unit is visible to a user looking through the second window of the lid. The display and window are both proximally located with the probe face and the second window distally located when the system is ready for use. With the second window in contact with tissue, the display faces away from the tissue so that the display, through the first window, can be seen by a user.

Figure 16:
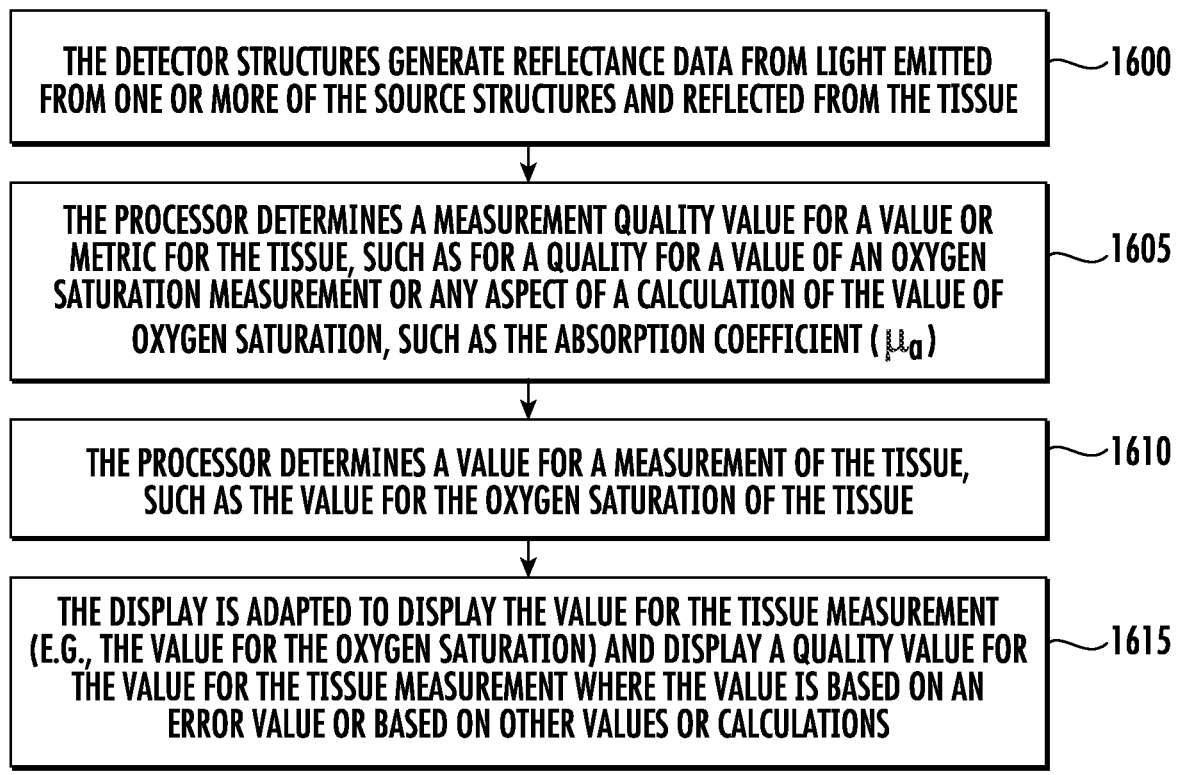
FIG. 16 shows a flow diagram of a method for determining and displaying a quality value on a display of the system unit in an implementation.

FIG. 16 shows a flow diagram of a method for determining and displaying a quality value on a display of the system unit 301 in an implementation. The quality metric controller 337 in combination with the processor and the other circuits of the system unit may operate the methods described. The flow diagram represents one example implementation. Steps may be added to, removed from, or combined in the flow diagram without deviating from the scope of the implementation.

At 1600, the detector structures (e.g., the photodetectors) generate reflectance data from light emitted from one or more of the source structures (e.g., LEDs) and reflected from patient tissue.

At 1605, the processor determines a measurement quality value for a value for the tissue, such as for a quality for a value of an oxygen saturation measurement or for any aspect or intermediate value of a calculation of the value of oxygen saturation, such as the absorption coefficient ($\mu_a$). The quality value can be calculated by any of the quality value calculations described below.

At 1610, the processor determines a value for a measurement of the tissue, such as the value for the oxygen saturation of the tissue.

At 1615, the display is adapted to display the value for the tissue measurement (e.g., the value for the oxygen saturation) and display a quality value for the tissue measurement where the quality value is based on an error value or based on other values or calculations.

FIG. 17 shows a flow diagram of a method for determining and displaying a quality value on system unit 301 in an implementation. The quality metric controller 337 in combination with the processor and the other circuits of the system unit may operate the methods described. The flow diagram represents one example implementation. Steps may be added to, removed from, or combined in the flow diagram without deviating from the scope of the implementation.

At 1700, the probe tip of the system unit contacts a patient's tissue, such as the tissue of a human patient. At 1705, the source structures of the probe tip emit light (e.g., infrared light) into the tissue.

At 1710, the light reflects from the tissue and is detected by the detector structures. At 1715, the detector structures generate reflectance data from the detected light. At 1720, the processor fits the reflectance data to simulated reflectance curves 315a stored in the memory of the system unit to determine a best fit of the reflectance data to the curves.

At 1725, the processor determines one or more measurement values of the tissue, such as a value for oxygen saturation, a value for blood volume, a value for the melanin concentration, or other measurement values based on the fit of the reflectance data to the simulated reflectance curves.

At 1730, the processor calculates a quality value for a value for the tissue, such as for a quality for a value of an oxygen saturation measurement or any aspect of a calculation of the value of oxygen saturation, such as the absorption coefficient ($\mu_a$). The quality value can be determined by the processor via comparison and assessment of the relationship between the reflectance at the detector structures and the reflectance data generated by the detector structures. This relationship can be based on raw data generated by the detector structures, filtered data, calibrated data, analog-to-digital (A-to-D) converter counts, or any other manipulation of the data. The quality value may be calculated by the processor based on relationships between two or more detector structures and one or more sources. The quality value may be calculated based on detector data from one source location (e.g., source structure 725a) versus another source location (e.g., source structure 725b).

In an implementation, the quality value is determined by comparing relationships between measurements, predictions, or both made at similar times. The measurements for the similar times can be for time points during a temporal series of oximeter measurements (e.g., three, four, five, six, or more oximeter measurements over a period of time when the measurements are made on tissue of a patient) where the measurements for the similar times are compared to each other. A particular oximeter measurement can be made in a number of microseconds, a number of milliseconds, or smaller or longer periods. The series of oximeter measurements can be for predictions of tissue parameters, such as values for oxygen saturation, values for relative oxygen saturation, or any calculated value used by the system unit for calculating a subsequent value, such as where the subsequent value is an oxygen saturation value or a relative oxygen saturation value on particular patient tissue) to one another. Noise in the oximeter measurements (e.g., formalized as a coefficient of variance in absorption predicted at a particular wavelength over the course of three oximeter measurements) is used by the system unit (e.g., an oximeter device) to adjust a first quality metric (e.g., that is based on an error versus the curve).

The quality value determined by the processor can be based on ratiometric calculations or ascertained by comparing data distributions (e.g., through methods similar to the Bhattacharyya or Mahalanobis distance). The quality value may also be calculated by the processor based on the temporally current relationship among detector structures compared with typical relationships among the detector structures, which are stored in memory 315. The quality value can be an error value for the fit of the reflectance data to one or more reflectance curves that best fit the data. The error value can be determined from one or more of a number of error fitting techniques, such as a least squares technique, a weighted least squares technique, a regularization technique, such as the Tikhonov regularization technique, the Lasso technique, or other techniques. The quality value can be the error value or can be derived from the error value. A "best" fitting or "closest" fitting simulated reflectance curve to reflectance data for a tissue measurement can be a simulated reflectance curve that has a smallest error value determined from one of the error fitting techniques or other error fitting techniques.

As described, a quality value for a given displayed value may be determined or calculated by one or more different techniques, or a combination of these. As an example, the quality value shown on the display may be a moving average value of multiple measurement samples of oxygen saturation or other values, intermediary values (e.g., the absorption coefficient $\mu_a$), aspects, calculations, intermediary calculations, or measurements used in determining a measured value, such as the oxygen saturation. The quality value gives an indication of how close the distribution (e.g., standard deviation or variance) of measured samples is to the moving average. The more closely the sampled measurements are grouped together and are close to the moving average, this indicates a higher quality measurement. In contrast, the less tightly spaced the samples are, the less quality of the measurement.

For example, in a first case, a first measurement is based on a distribution curve where one standard deviation is, for example, X percent from the average. In a second case, a second measurement is based on a distribution curve where one standard deviation is, for example, Y percent from the average. Y is greater than X. Then, when displaying the first measurement, the quality indicator will show a higher value than when displaying the second measurement.

At 1735, the processor controls the display to display the value for the measurement value (e.g., oxygen saturation value) and control the presentation of quality value for the displayed value. The quality values can be presented on the display as a percentage, via a bar graph displayed on the display, via lighted bar graph, via a color light emitting quality indicator, via a sound emitting quality indicator, via a dial gauge, or via other quality indicator.

Figure 18:
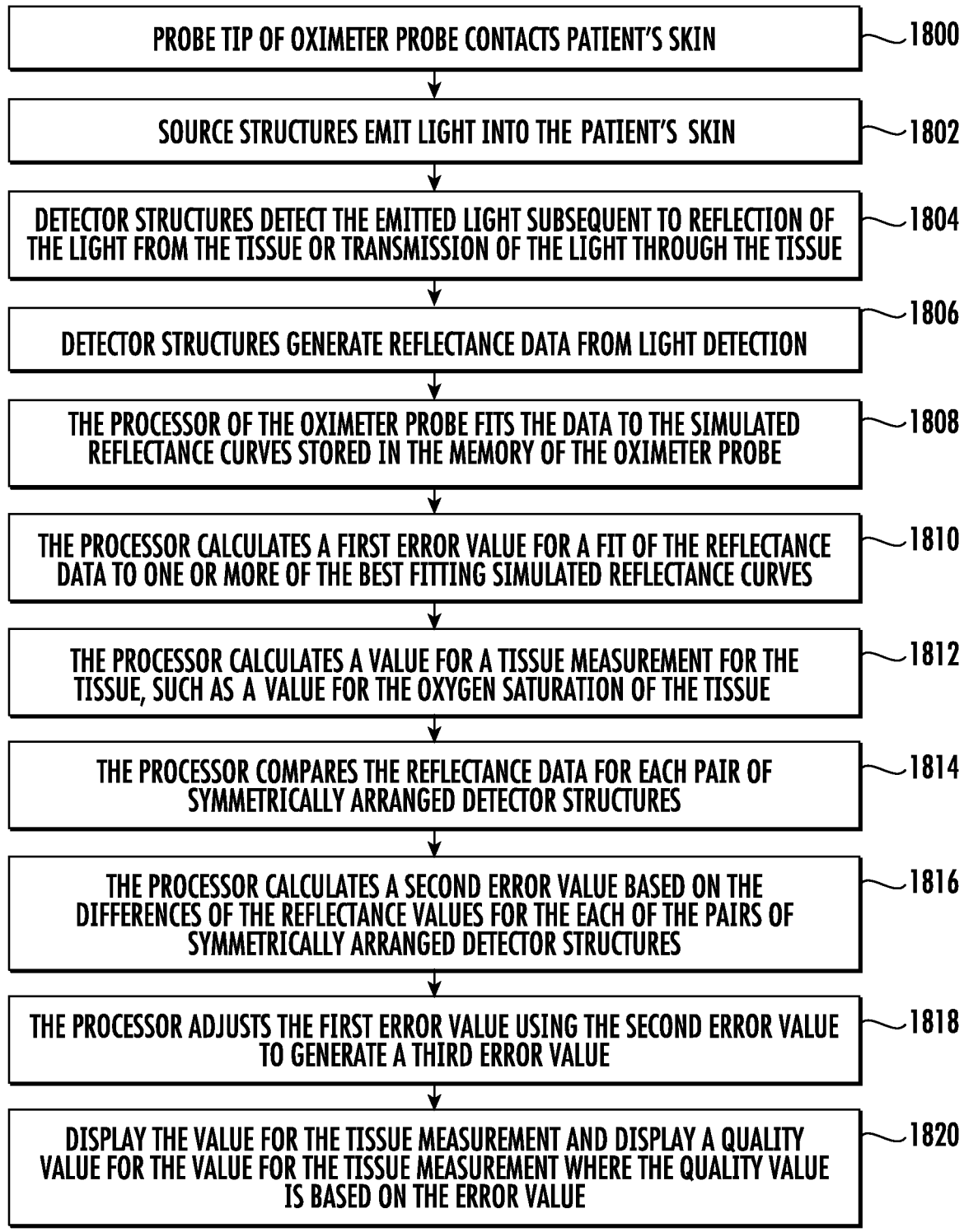
FIG. 18 shows a flow diagram of a method for determining inhomogeneity in oximeter measurements in an implementation.

FIG. 18 shows a flow diagram of a method for determining inhomogeneity in oximeter measurements in an implementation. The quality metric controller 337 in combination with the processor and the other circuits of the system unit may operate the methods described. The flow diagram represents one example implementation. Steps may be added to, removed from, or combined in the flow diagram without deviating from the scope of the implementation.

At 1800, the probe tip of the system unit contacts a patient's tissue, such as the tissue of a human patient. At 1802, the source structures of the probe tip emit light (e.g., infrared light) into the tissue. At 1804, the light reflects from the tissue and is detected by the detector structures.

At 1806, the detector structures generate reflectance data from the detected light.

At 1808, the processor fits the reflectance data to simulated reflectance curves 375 stored in the memory of the system unit to determine a best fit of the reflectance data to the curves.

At 1810, the processor calculates a first error value for the fit of the reflectance data to one or more reflectance curves that best fit the data. The fit can be performed for reflectance data generated by all of the detectors or one or more subsets of the detectors. For example, the fit can be performed for a first subset of detectors that are nearer than a threshold distance to one of the source structures, a second subset of detectors that are nearer than the threshold distance to another of the source structures, or both the first and second subsets. In another example, the fit can be performed for a third subset of detectors that are farther than a threshold distance from one of the source structures, a fourth subset of detectors that are farther than the threshold distance from another of the source structures, or both the third and fourth subsets. The error value can be determined from one or more of a number of error fitting techniques, such as a least squares technique, a weighted least squares technique, a regularization technique, such as the Tikhonov regularization technique, the Lasso technique, or other techniques.

At 1812, the processor determines one or more tissue measurement values of the tissue, such as the oxygen saturation, the blood volume, the melanin concentration, or other tissue measurement values based on the fit of the reflectance data to the simulated reflectance curves.

At 1814, the processor compares reflectance data for detector structures that are symmetrically located with respect to each other about a point on a line connecting source structures 725*a* and 725*b*. For example, in an implementation, detector structures 730*a* and 730*e* are symmetrically positioned about a point on a straight line connecting source structures 725*a* and 725*b*. Detector structures 730*b* and 730*f* are symmetrically positioned about the point. Detector structures 730*c* and 730*g* are symmetrically positioned about the point. Detector structures 730*d* and 730*h* are symmetrically positioned about the point. The point can be centered between source structures 725*a* and 725*b* on the connecting line.

The reflectance data for the detector structure can be compared for pairs of detectors. For example, the reflectance data can be compared for the pairs of symmetrically positioned detectors structures or other pairs of detector structures. More specifically, at step 1814, the processor compares reflectance data generated by detector structures 730*a* and 730*e*, compares reflectance data generated by detector structures 730*b* and 730*f*, compares reflectance data generated by detector structures 730*c* and 730*g*, and compares reflectance data generated by detector structures 730*d* and 730*h*.

The processor can alternatively compare one or more components derived from the reflectance data, such as the absorption coefficient derived from the reflectance data. The following described steps of the method may use the derived components for the method rather than, or in addition to the reflectance data.

At 1816, if the magnitudes of the reflectance data for two symmetrically positioned detector structures differ by a threshold reflectance amount or more, then the processor generates a second error value based on the difference in the reflectance data. The reflectance data might differ for two symmetrically positioned detector structures if the pressure applied to the probe type is not uniform across the face of the probe tip and the detector structures are positioned different distances away from the surface of the tissue as a result of the nonuniformly applied pressure. Differences in reflectance data can also occur for skin having varying skin color, such as skin with freckles or vitiligo.

At 1818, the processor adjusts the first error value using the second error value to generate a third error value. The first error value can be adjusted by the second error value via one or more of a variety of techniques including one or more arithmetic corrections, a functional correction, both of these corrections, or other corrections.

In some implementations, the first error value can be relatively high for skin that is relatively light or relatively dark. The tissue measurements (oxygen saturation measurements) made by the system unit for skin having these relatively light and dark skin colors can be more accurate than indicated by the first error value. Therefore, the adjustment to the first error value using the second error value can be applied by the processor for skin having these relatively light and dark colors.

At 1820, the processor controls the display to display the measurement value for the tissue parameter (e.g., oxygen saturation value) and control the presentation of quality value for the displayed value. The quality value can be the third error value or can be derived from the third error value. The quality values can be presented on the display as a percentage, via a bar graph displayed on the display, via a lighted bar graph, via a color light emitting quality indicator, via a sound emitting quality indicator, or via another quality indicator.

Figure 19:
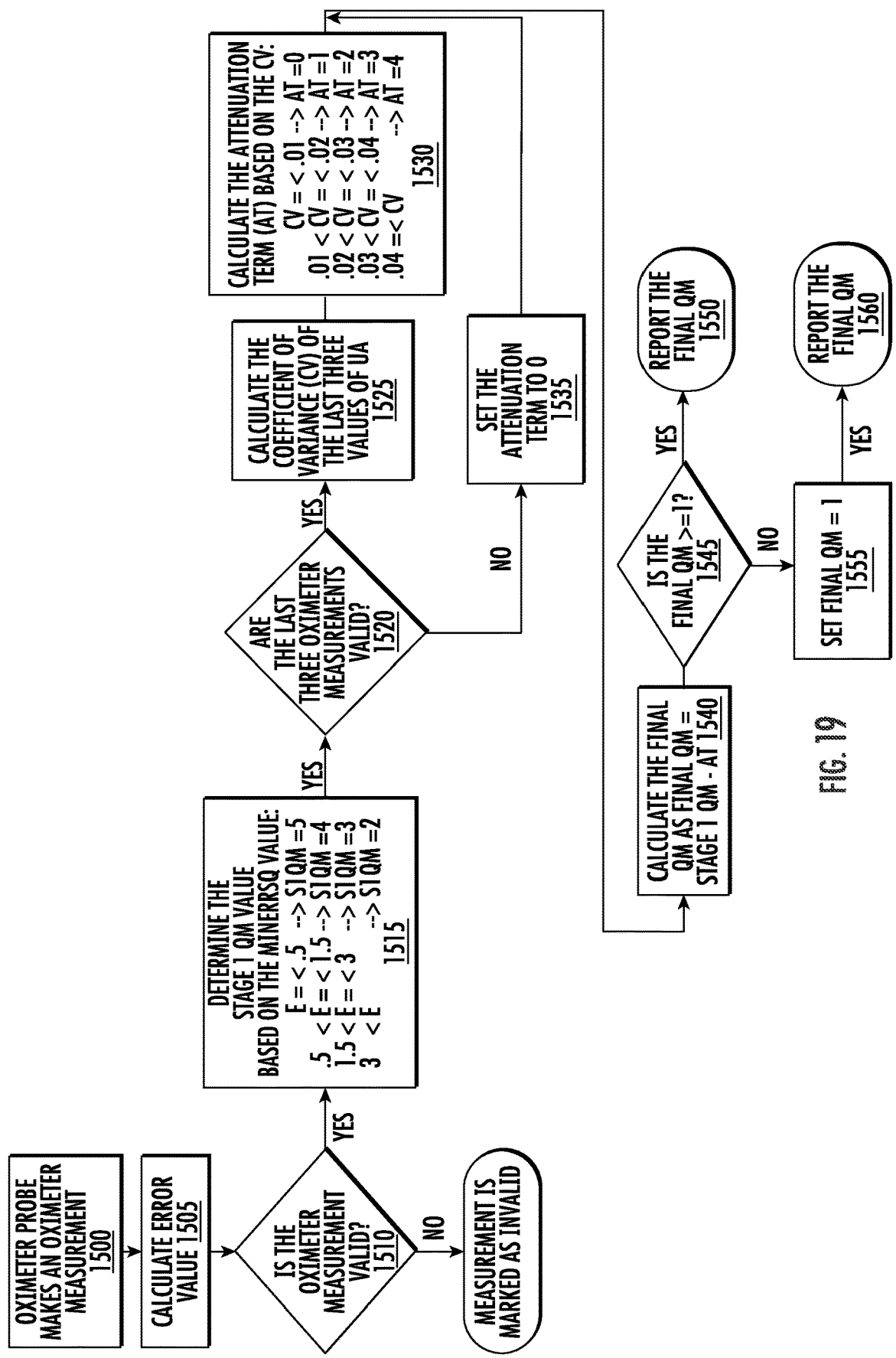
FIG. 19 shows a flow diagram of a method for determining a value for a quality measure (e.g., quality value) that indicates a degree of certainty of displayed oximetry measurements.

FIG. 19 shows a flow diagram of a method for determining a value for a quality measure (e.g., quality value) that indicates a degree of certainty of displayed oximetry measurements. The quality metric controller 337 in combination with the processor and the other circuits of the system unit may operate the methods described. The quality metric informs a user of the system unit (e.g., oximeter device whether the displayed values for oximetry measurements are accurate. The flow diagram represents one example implementation. Steps may be added to, removed from, or combined in the flow diagram without deviating from the scope of the implementation.

The method facilitates the display of an on-screen quality measure value in the range from 0-5,1-5,0-10, 1-10, or another range, to indicate the quality of displayed oximetry measurements to thereby aid users in determining whether the displayed oximeter measurements are acceptable and reliable.

More specifically, the quality metric provides an indication of the consistency of light detected between select detector structures or pairs of detector structures of the sensor probe (e.g., an oximetry probe).

As described above, a number of pairs of detector structures include the first and second detector structures that are equidistant from the first and second source structures, respectively. In the example of FIG. 9, detector structure 730*a* and 730*e* are equally distant from source structures 725*a* and 725*b*, respectively, as are other pairs of the detector structures (e.g., 730*b* and 730*f*; 730*c* and 730*g*; and 730*d* and 730*h*) with respect to the first and second source structures 725*a* and 725*b*. Higher equality of light detected by two detector structures that are equidistant from the source structures are described as having higher quality values and lower equality of light detected by the two detector structures are described as having lower quality values.

The loss of light in tissue being measured should be equal at first and second detector structures of a pair of detectors that are equidistance from the first and second source structures, respectively. Deviation from detection of equal loss of light from tissue can indicate one or more modes (e.g., two modes) of loss of light from equality. A first mode of deviation from equality is associated with one of the first and second detector structures being above the tissue surface or the two detector structures being placed on the tissue surface with different pressure.

According to an implementation, memory 315 stores a number of Monte-Carlo-simulated reflectance curves 315a ("simulated reflectance curves"), which may be generated by a computer for subsequent storage in the memory. Each of the simulated reflectance curves 315a represents a simulation of light (e.g., near-infrared light) emitted from one or more simulated source structures into simulated tissue and reflected from the simulated tissue into one or more simulated detector structures. Simulated reflectance curves 315a are for a specific configuration of simulated source structures and simulated detector structures, such as the configuration of source structures 725a-725b and detector structures 730a-730h of probe tip 338 having the source-to-detector spacing described above with respect to FIG. 9.

Therefore, simulated reflectance curves 315a model light emitted from the source structures and collected by the detector structures of system unit 301. Further, each of the simulated reflectance curves 315a represents a unique real tissue condition, such as specific tissue absorption and tissue scattering values that relate to particular concentrations of tissue chromophores and particular concentrations of tissue scatterers. For example, the simulated reflectance curves can be generated for simulated tissue having various melanin contents, various oxygenated hemoglobin concentrations, various deoxygenated hemoglobin concentrations, various concentrations of water, a static value for the concentrations of water, various concentrations of fat, a static value for the concentration of fat, or various absorption ($\mu_a$) and reduced scattering ($\mu_s'$) values.

The number of simulated reflectance curves stored in memory 315 may be relatively large and can represent nearly all, if not all, practical combinations of optical properties and tissue properties that may be present in real tissue that is analyzed for viability by system unit 301. While memory 315 is described as storing Monte-Carlo-simulated reflectance curves, memory 315 may store simulated reflectance curves generated by methods other than Monte-Carlo methods, such as using a diffusion approximation.

Figure 20:
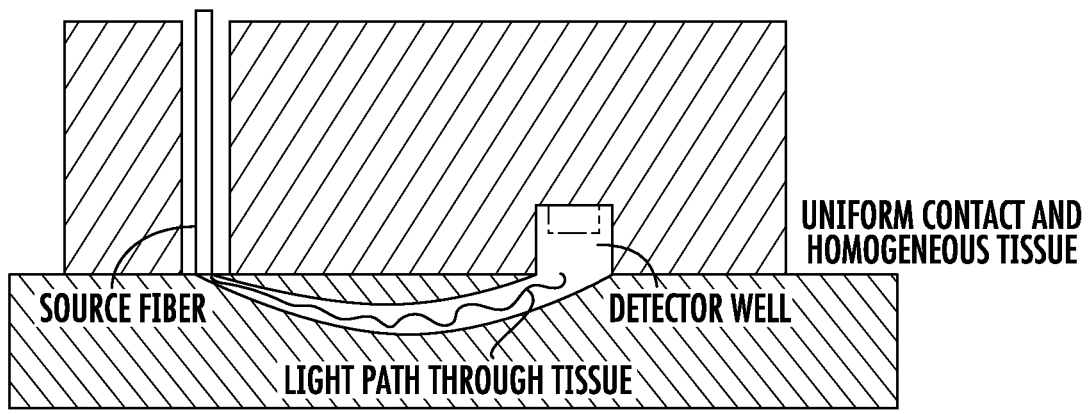
FIGS. 20 and 21 show first and second detectors where one of the detectors is in contact with the tissue and the second detector is above the surface of the tissue.
Figure 21:
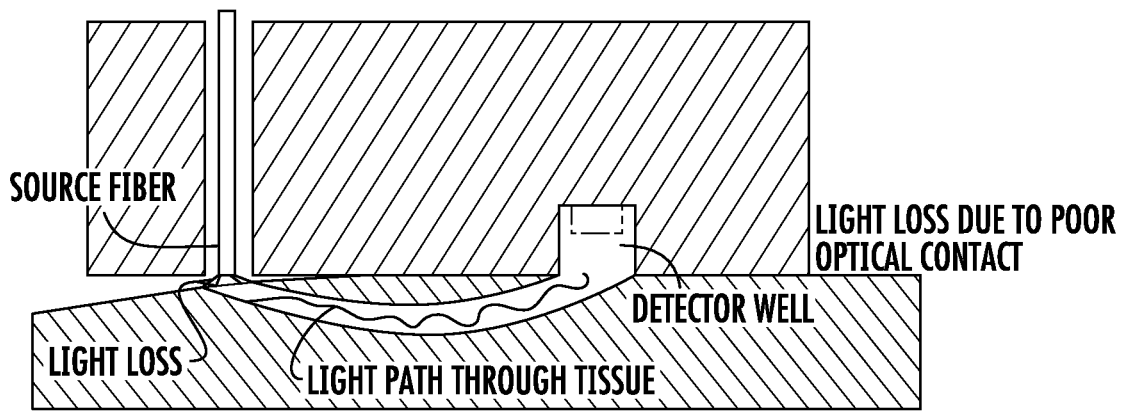

FIGS. 20 and 21 show first and second detectors where one of the detectors is in contact with the tissue and the second detector is above the surface of the tissue. The first and second detectors are equidistant from the first and second sources, respectively.

Figure 22:
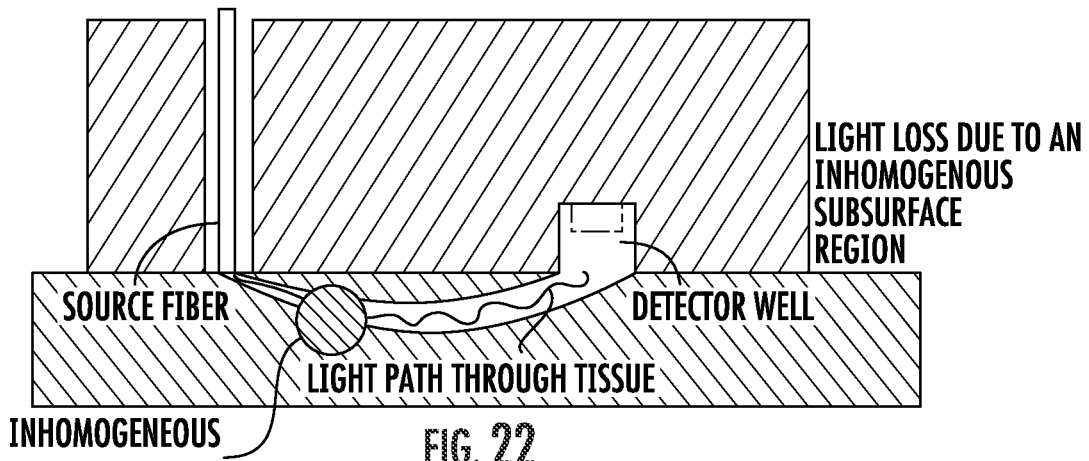
FIG. 22 shows the two light paths with an inhomogeneity of tissue region along the light path.
Figure 23:
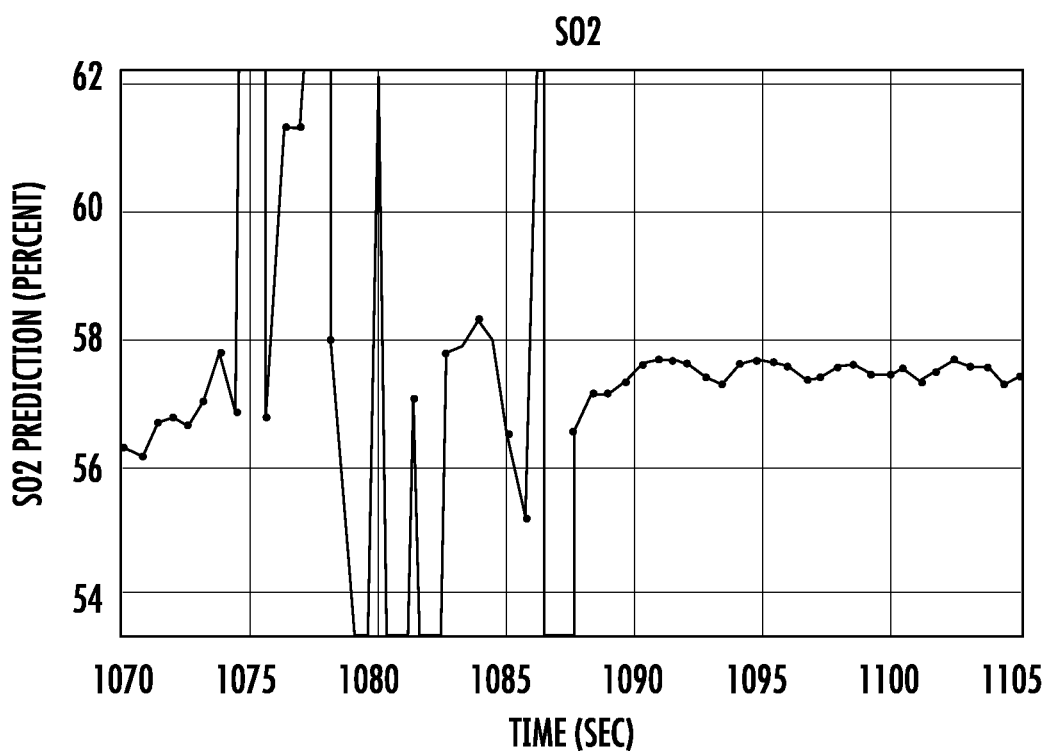
FIGS. 23-26 show graphs of oximeter measurements for StO2, the Minerrrsq value (described below), mua, and mua prime.
Figure 24:
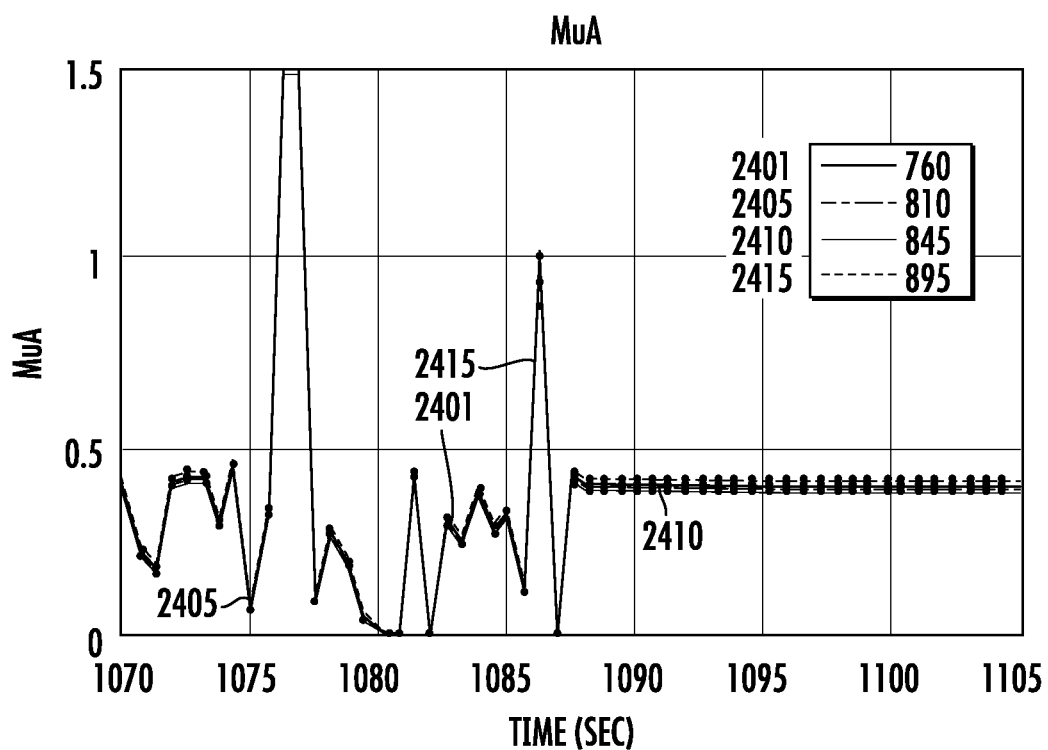
Figure 25:
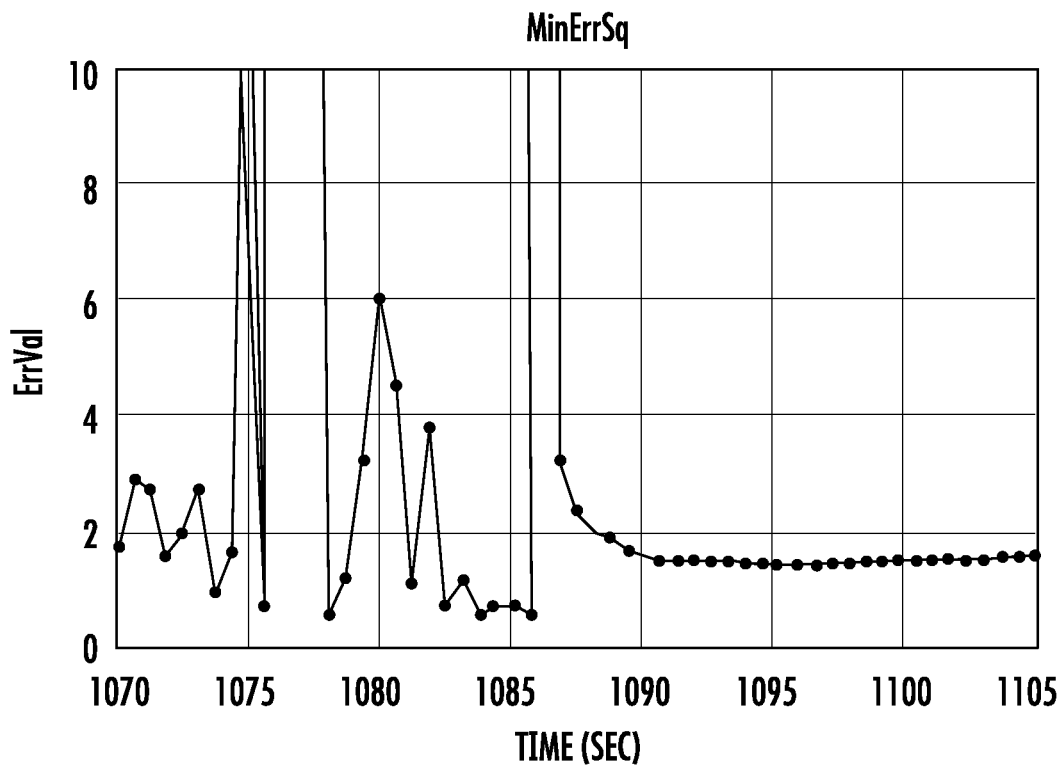
Figure 26:
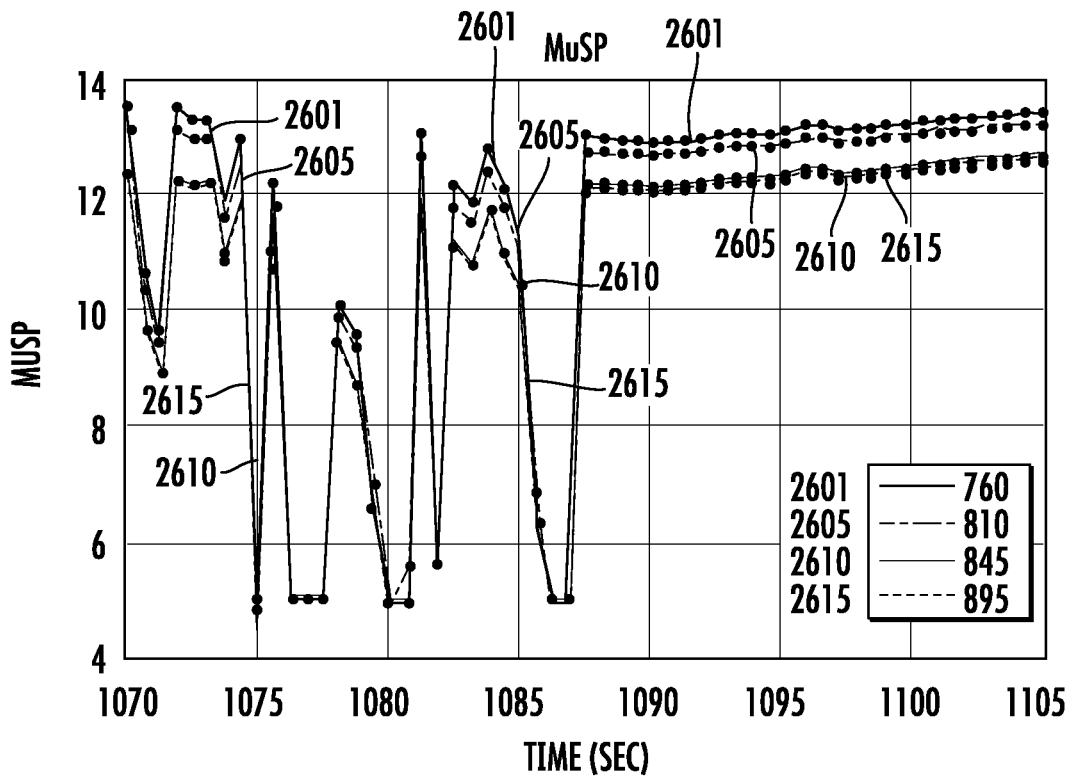

A second mode of deviation from equality of light detection by the first and second detectors is associated with an inhomogeneity in the subsurface region of the tissue. Specifically, between two light paths between the first detector and the first source (first light path) and between the second detector and the second source (second light path) where the paths are equidistant, the inhomogeneity is in one of the two light paths. FIGS. 20 and 22 show the two light paths with an inhomogeneity of tissue region along the light path of FIG. 22.

In an implementation, the quality measure is calculated by two steps as further described below. In a first step, a "stage 1" quality measure (QM) is determined based on the error values. Low error values correspond to high stage 1 QM values, whereas higher error values (e.g., lower than the low error values) correspond to lower stage 1 QM values (e.g., lower than the high stage 1 QM values).

In a second step, an adjustment for the stage 1 QM values is determined. The adjustment for the stage 1 QM in the second step is based on an artifact created in the first step associated with noise associated with unstable contact (i.e., movement) of the probe tip for a conditioned favored by the first step where the probe tip is positioned 1 millimeter or approximately 1 millimeter (e.g., 0.25 millimeters to 0.5 millimeters) above the tissue surface. The stage 1 QM values may be adjusted by a multiplier or a summed term.

FIGS. 23-26 show graphs of oximeter measurements for StO2, the Minerrrsq value (described below), mua, and mus prime. The approximate left half of each graph shows the parameters for unstable contact between the probe face and tissue and the approximate right half of the graphs shows the parameters for stable contact. The first and second steps are presently further described.

At 1500, the oximeter probe makes an oximeter measurement when the oximeter probe being is contacted to a patient's tissue, such as the tissue of a human patient. The source structures of the probe tip emit light (e.g., visible light, infrared light, or both) into the tissue. The light reflects from the tissue and is detected by the detector structures. The detector structures generate reflectance data from the detected light. The processor fits the reflectance data to simulated reflectance curves 375 stored in the memory of the oximeter probe to determine a best fitting one or more of the simulated reflectance curves to the reflectance data. A best fitting simulated reflectance curve to the data can be a fit that has a lowest error value determined by a fitting algorithm, such as a minimum error square, a least squares technique, a weighted least squares technique, a regularization technique, such as the Tikhonov regularization technique, the Lasso technique, or other techniques.

At 1505, the processor calculates the error value for the fit of the reflectance data to one or more reflectance curves that best fit the data. In an implementation where a minimum error square techniques is used, the error value is a minimum error square value ("MinErrSq" value).

At 1510, the processor compares the error value to an error threshold hold value to determine whether the oximeter measurement is valid. If the error value is less than the error threshold value, then the oximeter measurement is valid. If the error value is equal to or greater than the error threshold value, then the oximeter measurement is not valid. In an embodiment, other errors can render an oxygen saturation value invalid.

If the oximeter measurement is determined to be valid, then the error value (e.g., the MinErrSq value) is mapped (e.g., converted) from a range of error values in which the error values lie to a value that represents the range. See 1515 in FIG. 19. The values that represent ranges of error values are referred to as stage 1 quality measure (QM) values. In an implementation, the MinErrSq values are whole numbers or fractional values and the stage 1 QM values are integers.

The mapping can be determined from a lookup table, can be calculated from the error values, or otherwise determined. Table A below shows an example lookup table that might be used for converting the MinErrSq values to the stage 1 QM values.

TABLE A

| Equality Relationship of MinErrSq Value | Stage 1 Quality Measure (QM) |
|---|---|
| First range of error values: MinErrSq value is less than or equal to 0.5; (value < or = 0.5) | 5 |

TABLE A-continued

| Equality Relationship of MinErrSq Value | Stage 1 Quality Measure (QM) |
|---|---|
| Second range of error values: If MinErrSq value is greater than 0.5 and less than or equal to 1.5 (e.g., 0.5 < value <= 1.5) | 4 |
| Third range of error values: If MinErrSq value is greater than 1.5 and less than or equal to 3.5 (e.g., 1.5 < value <= 3) | 3 |
| Fourth range of error values: If MinErrSq value is greater than 1.5 | 2 |

Table A shows that the four ranges of error values are mapped to four integer stage 1 QM values. In other implementations, more or fewer ranges and stage 1 QM values are used. Further, the width of the ranges of the MinErrSq values is different (e.g., wider ranges or narrower ranges) in other implementations. Further, the integer values (e.g., 2, 3, 4, and 5) are different in other implementations.

The stage 1 QM values are quality measure values that incorporate error effects from (i) uneven contact of the probe face of the oximeter probe with the tissue, (ii) asymmetric pressure of the probe face on the tissue, (iii) local inhomogeneity of the tissue, and (iv) uneven tissue surface.

At 1520, the processor determines whether a number (e.g., 3 or another number of prior oximeter measurements) of the prior oximeter measurements are valid or not valid. The number of other oximeter measurements can be measurement made prior to the current oximeter measurement being described, can include the current oximeter measurement being described, can be oximeter measurements made before and after the current oximeter measurement being described, or can be oximeter measurements made after the current oximeter measurement being described.

If the number (e.g., 3) of the prior oximeter measurements are valid, then the processor calculates a coefficient of variance value for the last numbers (e.g., 3) of absorption coefficients values for the last numbers (e.g., 3) oximeter measurements for a particular wavelength transmitted by the source structures of the oximeter probe. In an implementation, the wavelength is 859 nanometers. The coefficient of variance value can be the standard deviation divided by the mean for the $\mu_a$ values for 810 nanometers.

The coefficient of variance value can be calculated according to: $CV=(\Sigma(\mu_a-\text{average}(\mu_a))/(n-1))^{1/2}/\text{average}(\mu_a)$. The average $\mu_a$ can be for the last number (e.g., 3) of $\mu_a$ for the last number of oximeter measurements. See 1525 of FIG. 19.

The CV value is thereafter converted into an attenuation term (AT) value. The CV value can be converted into the AT value via a lookup table (e.g., database) that stores the conversion information. Table B below is an example lookup table used for converting the CV value into the AT value. See 1530 of FIG. 19.

TABLE B

| Coefficient of Variance Values | Attenuation Term Values |
|---|---|
| First range of CV values: CV value is less than or equal to 0.01; (value < or = 0.01) | 0 |
| Second range of CV values: If CV value is greater than 0.01 and less than or equal to 0.02 (e.g., 0.01 < value <= 0.02) | 1 |
| Third range of CV values: If CV value is greater than 0.02 and less than or equal to 0.03 (e.g., 0.02 < value <= 0.03) | 2 |
| Fourth range of CV values: If CV value is greater than 0.03 and less than or equal to 0.04 (e.g., 0.03 < value <= 0.04) | 3 |
| Fifth range of CV values: If CV value is greater than 0.04 (e.g., value < 0.04) | 4 |

If the number of the prior oximeter measurements are not valid, then the processor of the system unit, sets the AT value to zero. See 1535 of FIG. 19. In an alternative implementation, if the number of the prior oximeter measurements are not valid, then the processor of the system unit, the system unit displays the value for the stage 1 QM on the display. For example, the stage 1 QM value 2, 3, 4, or 5 (or others if other numbers are used) is displayed on the display based on the MinErrSq value.

At 1540, the processor calculates a further quality measure (QM), which can be a final QM. The final QM can be calculated as: final QM=Stage 1 QM−AT.

If the processor determines that the final QM value is greater than or equal to 1 (e.g., final QM>=1), then the calculated final QM value is displayed on the display. See 1545 and 1550 in FIG. 19.

If the processor determines that the final QM value is not greater than or equal to 1, then the final QM value set to 1, and this final QM value 1 is displayed on the display. See 1555 and 1560 in FIG. 19. When the final QM is not greater or equal to 1, a possibility exists that the AT value is greater than the final QM value, and the determination of final QM=Stage 1 QM−AT can yield a negative value for the final QM. Rather than report a negative value for final QM, the final QM is set to 1 at 1555.

Figure 27:
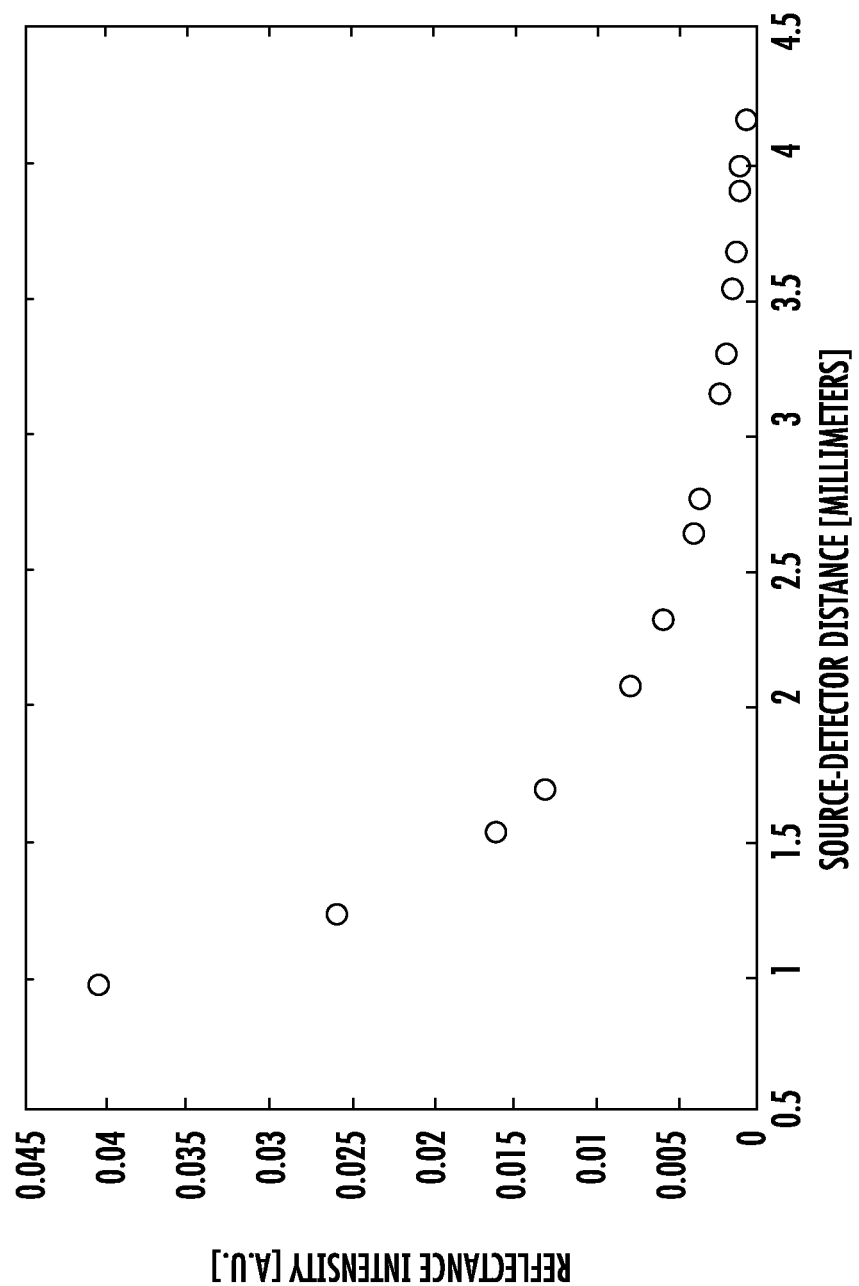
FIG. 27 shows an example graph of a reflectance curve, which may be for a specific configuration of the source structures and detector structures, such as the configuration source structures and detector structures of the probe tip.

FIG. 27 shows an example graph of a reflectance curve, which may be for a specific configuration of source structures 725a-725b and detector structures 730a-730h, such as the configuration source structures and detector structures of probe tip 338. The horizontal axis of the graph represents the distances between source structures 725a-725b and detector structures 730a-730h (i.e., source-to-detector distances). If the distances between source structures 725a-725b and detector structures 730a-730h are appropriately chosen, and the simulated reflectance curve is a simulation for source structures 725a-725b and detector structures 730a-730h, then the lateral spacings between the data points in the simulated reflectance curve will be relatively uniform. Such uniform spacings can be seen in the simulated reflectance curve in FIG. 16. The vertical axis of the graph represents the simulated reflectance of light that reflects from tissue and is detected by detector structures 730a-730h. As shown by the simulated reflectance curve, the reflected light that reaches detector structures 730a-730h varies with the distance between source structures and detectors structures, with the reflected light detected at smaller source-to-detectors distances greater than the reflected light detected a larger source-to-detector distance.

FIG. 28 shows a graph of the absorption coefficient $\mu_a$ versus wavelength of light for some significant tissue chromophores: blood containing deoxygenated hemoglobin 2801, blood containing oxygenated hemoglobin 2805, melanin 2810, water 2815, and fat 2820. In an implementation, the Monte-Carlo simulations used for generating the simulated reflectance curve are functions of one or more select chromophores that may be present in tissue. The chromophores can include melanin, oxygenated hemoglobin, deoxygenated hemoglobin, water, lipid, cytochrome, or other chromophores, in any combination. Oxygenated hemoglobins, deoxygenated hemoglobins, and melanin are the dominant chromophores in tissue for much of the visible and near-infrared spectral range.

In an implementation, memory 315 stores a select number of data points for each of the simulated reflectance curves 315a and might not store the entirety of the simulated reflectance curves. The number of data points stored for each of the simulated reflectance curves 315a may match the number of source structure detector structure (source-detector) pairs. For example, if probe tip 338 includes two source structures 725a-725b and includes eight detector structures 730a-730h, then system unit 301 includes sixteen source-detector pairs, and memory 315 may thus store sixteen select data points for each of the simulated reflectance curves for each wavelength of light emitted by source structure 725a or source structure 725b. In an implementation, the stored data points are for the specific source structure-to-detector structure distances of probe tip 338.

Thus, the simulated reflectance curve database stored in memory 315 might be sized 16×5850 where sixteen points are stored per curve that may be generated and emitted by each source structure 725a-725b and measured by each detector structure 730a-730h, where there are a total of 5850 curves spanning the optical property ranges. Alternatively, the simulated reflectance curve database stored in memory 315 might be sized 16×4×5850 where sixteen points are stored per curve for four different wavelengths that may be generated and emitted by each source structure and where there are a total of 5850 curves spanning the optical property ranges. The 5850 curves originate, for example, from a matrix of 39 scattering coefficients $\mu_s'$ values and 150 absorption coefficient $\mu_a$ values. In other implementations, more or fewer simulated reflectance curves are stored in the memory. For example, the number of simulated reflectance curves stored in memory can range from about 5000 curves, to about 250,000 curves, to about 400,000 curves, or more.

In an embodiment, each simulated reflectance curve is stored in a four-dimensional table where values for the reflectance intensity (e.g., in arbitrary units) and the source-detector distance are stored with the reduced scattering coefficients $\mu_s'$ as the scattering coefficient $\mu_s$ and the anisotropy g, where $\mu_s'=\mu_s(1-g)$. That is, the reduced scattering coefficient is stored as two values in a four-dimensional table for a simulated reflectance curve. The anisotropy g is the expectation value for the cosine of the average scattering angle g=cos($\theta$) for the average scattering angle of the light (e.g., visible, IR, or both) in tissue.

The reduced scattering coefficient $\mu_s'$ values might range from 2.5:2.5:21.5 per centimeter. The $\mu_a$ values might range from 0.01:0.01:1.5 per centimeter. It will be understood that the foregoing described ranges are example ranges and the number source-detector pairs, the number of wavelengths generated and emitted by each source structure, and the number of simulated reflectance curves may be smaller or larger.

In an implementation, a quality value is used to generate a value for the stability of an oximetry value, such as a value for oxygen saturation StO2.

U.S. patent application Ser. No. 15/495,194, filed Apr. 24, 2017, describes the determination of the quality metric, modification of the quality metric, and qualification of the quality metric, and is incorporated by reference along with all references cited in these applications In an implementation, the quality metric and any of the described modifications or qualifications of the quality metric are determined while the system unit is located in the sheath. Thus, the quality metric is a quality metric for the system unit operating in the sheath. That is, the quality metric is a quality metric for transmission of light from the system unit through the second sheath window of the sheath, collection of the light after reflection from tissue through the second sheath window of the sheath and the system unit. The quality metric is a quality metric for the second sheath window angled at various angles with respect to tissue to be measured. That is, a portion of the second sheath window of the sheath may be out of contact with tissue to be measured or a portion of the second sheath window may be pressed with less pressure onto tissue than another portion of the second sheath window. Such contact and non-contact moves portions of the source structures, detector structures, or both relatively closer to tissue being measure than other portions of the source structures, detector structures, or both, which are farther from the surface of tissue being measured. As described above, the difference in distances of source structures, detector structures, or both affects the value of the quality metric from loss of light from the source structures, at the detector structures, or both. The difference in distances between the surface of the tissue and a source structure or a detector structure (e.g., angular misorientation) also causes uneven pressure to be applied to the tissue surface, which affects the quality metric from capillary occlusion. That is, when more pressure from one side of the probe is applied to the tissue than another side of the probe face, the tissue has a tendency to bleach unevenly across the pressure gradient applied by the sheath or system unit (e.g., is the system unit is used without the sheath), which can affect the quality of the oximeter measurements and the quality metric for these measurements.

Therefore, the angular orientation of the second sheath window with tissue being measured, affects the quality metric.

In an implementation, the described modifications and qualifications of the quality metric are modifications and qualifications of the quality metric for the system unit operating in the sheath. That is, the described modifications and qualifications of the quality metric are modification and qualifications of the quality metric for transmission of light from the system unit through the second sheath window of the sheath, collection of the light after reflection from tissue through the second sheath window of the sheath and the system unit.

In an implementation, the QM module and the processor operate with the accelerometer to scale, modify, qualify, characterize, or any combination of these operations the quality metric. The accelerometer can detect whether the system unit and sheath shake in a user's hand while oximetry measurements are made by the system unit. Shaking can angle the probe face and the sheath window with respect to tissue being measured, which can raise or lower the quality of an oximetry reading. The shaking has a frequency. The QM module, the processor, or both can use movement information generated by the accelerometer in response to the movement of the system unit and sheath to adjust the quality metric to indicate an unchanged quality metric, an improved quality metric, or a decreased quality metric. The processor can adjust the quality metric based on the frequency of the shaking. For example, the adjustment to the quality metric can be adjusted proportionally to the frequency of the shaking. The quality metric can be adjusted by the processor based on the length (e.g., the average length, maximum length, minimum length, or another length) of movement from the shaking.

In an implementation, the accelerometer, the detector structures using light collected by the detector structures, a pressure sensor, or other elements of the system unit or sheath, when the system unit is in the sheath, measure the angular orientation of the second sheath window with respect to tissue being measured. The QM module, the processor or both use the angular orientation information to adjust or qualify the quality metric. The processor can adjust the quality metric based on the angle of tilt detected by the accelerometer relative to the tissue. For example, the angle is used for a proportional (e.g., multiplier) adjustment to the quality metric.

The quality metric can be adjusted based on a length of movement that the oximeter device has moved relative to the tissue (away from the tissue, across the tissue, or a combination of these movement lengths). The processor can adjust the quality metric based on the length of the movement. For example, the length is used for a proportional (e.g., multiplier) adjustment to the quality metric.

The qualify metric can be adjusted based on the direction of movement. A first correction can be applied for movement across the tissue (x-direction, y-direction, or both). A second correction can be applied for movement away from the tissue (z-direction). A third correction can be applied for movement toward the tissue (minus z-direction). The levels of the first, second, and third correction can be different. For example, the levels of correction may be different for the same lengths of movement across the tissue, upward from the tissue, and towards the tissue.

In an implementation, the accelerometer detects movement if the movements persists for about 200 to about 400 milliseconds. In an implementation, the accelerometer detects movement if the movements persists for about 320 milliseconds. And any movement below the acceleration of the earth's gravity is detected (e.g., above about 9.8 meters/second squared).

In an implementation, the processor does not recognize movement of the system unit if the signal generated by the accelerometer is below a first threshold value (e.g., a first threshold voltage or a first threshold current). The processor may apply a first correction to the quality metric value for accelerometer output values (e.g., output voltages) above the first threshold value and below a second threshold value.

The processor may apply a second correction to the quality metric value for accelerometer output values (e.g., output voltages) above the second threshold value and below a third threshold value. The first and second corrections are different corrections where the second correction is larger than the first correction. The processor may apply a third correction to the quality metric value for accelerometer output values (e.g., output voltages) above the third threshold value and below a fourth threshold value. The second and third corrections are different corrections where the third correction is larger than the second correction. The processor may apply a fourth correction to the quality metric value for accelerometer output values (e.g., output voltages) above the fourth threshold value and below a fifth threshold value. The third and fourth corrections are different corrections where the fourth correction is larger than the third correction. The device may use additional threshold levels for an increasing amount of corrections, such a sixth, a seventh, an eighth, a ninth, or higher number of threshold levels.

In an embodiment, the accelerometer outputs information coordinate information for movement in a coordinate system, such as the Cartesian coordinate system. The output information may stored in an accelerometer register and transmitted to the processor for processing. The output information distance information for the distance the system unit has moved along one of the coordinate axes (e.g., Cartesian, polar, cylindrical, spherical, or others). The coordinate information output from the accelerometer is digital information In an implementation, processor adjust the quality metric value based on a number of guard bands that are determined based on the information output by the accelerometer. There may be two or more guard bands that the processor determines based on the accelerometer output. In an implementation, there are five guard bands that the processor determines based on the accelerometer output. Based on the particular guard band of movement that the system unit experiences and the accelerometer transfers to the processor, the processor can subtract out from between zero to about four points from the quality metric value at the stage 1 quality metric (described above).

The adjusted or qualified quality metric can be displayed on the display of the system unit. The QM module, processor, or both can also use the quality metric to adjust reported oximetry measurements. The above described methods for generating the quality metric can be modified to take into account acceleration information generated by the accelerometer or the described angle information. The modifications can include arithmetic modifications (e.g., a multiplier) of the quality metric based on acceleration information, angle information, or both. The modification can include using the acceleration information, angle information, or both in one or more other functions for calculating the quality metric, such as the function used for calculating the MinErrSq value.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
emitting light from at least one source of an oximeter device into a tissue to be measured, wherein the oximeter device comprises a nonvolatile memory that stores simulated reflectance curves and the nonvolatile memory retains the simulated reflectance curves even after the device is powered off;
receiving at a plurality of detectors of the oximeter device light reflected from the tissue in response to the emitted light;
generating, by the detectors, a plurality of detector responses from the reflected light;
fitting the detector responses to the simulated reflectance curves stored in the nonvolatile memory to determine an absorption coefficient value for the tissue;
calculating an oximetry value for the tissue from the absorption coefficient value;

based on the absorption coefficient value, calculating a quality metric value for the oximetry value;

detecting, by an accelerometer of the oximeter device, a movement of the oximeter device;

adjusting the quality metric value based on the detected movement of the oximeter device to generate an adjusted quality metric value; and displaying, by a processor on a display of the oximeter device, the oximetry value and the adjusted quality metric value for the oximetry value.

2. The method of claim 1 wherein the detecting, by the accelerometer of the oximeter device, the movement of the oximeter device comprises detecting a frequency of the movement, and the adjusting the quality metric value based on the detected movement of the oximeter device generates an adjusted quality metric value comprises adjusting the quality metric based on the frequency.

3. The method of claim 2 wherein the quality metric value is adjusted proportionally to the frequency.

4. The method of claim 1 wherein the detecting, by the accelerometer of the oximeter device, the movement of the oximeter device comprises detecting an angular movement of the oximeter device, and the adjusting the quality metric value based on the detected movement of the oximeter device to generate an adjusted quality metric value comprises adjusting the quality metric value based on an angle of the angular movement.

5. The method of claim 1 wherein the detecting, by the accelerometer of the oximeter device, the movement of the oximeter device comprises detecting a length of the movement of the oximeter device relative to the tissue, and the adjusting the quality metric value based on the detected movement of the oximeter device to generate an adjusted quality metric value comprises adjusting the quality metric value based on the length of the movement.

6. The method of claim 1 wherein the oximetry value is an oxygen saturation value for the tissue.

7. The method of claim 1 wherein the oximetry value is an absorption coefficient value for the tissue.

8. The method of claim 1 wherein the quality metric value is a moving average value of quality metric values.

9. The method of claim 1 wherein displaying the quality metric value comprises displaying the quality metric value as a percentage value via a bar graph.

10. A method comprising:
providing a tissue oximeter device comprising a nonvolatile memory storing simulated reflectance curves, wherein the nonvolatile memory retains the simulated reflectance curves even after the device is powered off;

emitting light from at least one source of the tissue oximeter device into a tissue to be measured;

receiving at a plurality of detectors of the tissue oximeter device light reflected from the tissue in response to the emitted light;

generating, by the detectors, a plurality of detector responses from the reflected light;

fitting the detector responses to the simulated reflectance curves stored in the nonvolatile memory to determine a plurality of absorption coefficient values for the tissue for a plurality of oximeter measurements;

calculating an oximetry value for the tissue from a first absorption coefficient value of the plurality of absorption coefficient values for a first oximeter measurement of the plurality of oximeter measurements;

based on the first absorption coefficient value of the plurality of absorption coefficient values, calculating a first quality metric value for the oximetry value for the first oximeter measurement using an error of the fitting of the detector responses to at least one of the simulated reflectance curves stored in the nonvolatile memory;

calculating a second quality metric value based on the first quality metric value and at least a second absorption coefficient value of the plurality of absorption coefficient values for at least a second oximeter measurement;

detecting, by an accelerometer of the oximeter device, an angular movement of the oximeter device when the light is emitted and when the light is detected;

receiving at a plurality of detectors of the tissue oximeter device light reflected from the tissue in response to the emitted light;

adjusting the second quality metric value based on the angular movement of the oximeter device to generate an adjusted quality metric value proportional to an angle of the angular movement; and displaying on a display of the oximeter device, the oximetry value and the adjusted quality metric value for the oximetry value.

11. The method of claim 10 wherein calculating the second quality metric value is based on the first quality metric value, the second absorption coefficient value of the plurality of absorption coefficient values for the second oximeter measurement, and a third absorption coefficient value of the plurality of absorption coefficient values for a third oximeter measurement.

12. The method of claim 10 wherein the second quality metric value is based on a time average of the first, second, and third absorption coefficient values for the first, second, and third oximeter measurements.

13. The method of claim 10 wherein the detecting, by the accelerometer of the oximeter device, the movement of the oximeter device comprises detecting a frequency of the movement, and the adjusting the quality metric value based on the detected movement of the oximeter device generates an adjusted quality metric value comprises adjusting the quality metric based on the frequency.

14. The method of claim 13 wherein the quality metric value is adjusted proportionally to the frequency.

15. The method of claim 10 wherein the detecting, by the accelerometer of the oximeter device, the movement of the oximeter device comprises detecting a length of the movement of the oximeter device relative to the tissue, and the adjusting the quality metric value based on the detected movement of the oximeter device to generate an adjusted quality metric value comprises adjusting the quality metric value based on the length of the movement.

16. The method of claim 10 wherein the oximetry value is an oxygen saturation value for the tissue.

17. The method of claim 10 wherein the oximetry value is an absorption coefficient value for the tissue.

18. The method of claim 10 wherein the quality metric value is a moving average value of quality metric values.

19. The method of claim 10 wherein displaying the quality metric value comprises displaying the quality metric value as a percentage value via a bar graph.

* * * * *